United States Patent [19]
Tanzawa

[11] Patent Number: 5,827,743
[45] Date of Patent: Oct. 27, 1998

[54] SUPPORT FOR GROWING/REGENERATING PLANT AND METHOD OF GROWING/REGENERATING PLANT

[75] Inventor: Hiroshi Tanzawa, Kamakura, Japan

[73] Assignee: Mukoyama Orchids Ltd., Yamanashi, Japan

[21] Appl. No.: 776,617

[22] PCT Filed: Jun. 20, 1995

[86] PCT No.: PCT/JP95/01223

§ 371 Date: Dec. 20, 1996

§ 102(e) Date: Dec. 20, 1996

[87] PCT Pub. No.: WO95/35025

PCT Pub. Date: Dec. 28, 1995

[30] Foreign Application Priority Data

Jun. 21, 1994 [JP] Japan ................................. 6-139140

[51] Int. Cl.$^6$ ............................ A01G 31/00; A01H 4/00; C12M 3/00
[52] U.S. Cl. .............................. 435/430; 435/431; 47/44; 47/58; 47/48.5
[58] Field of Search .................................. 435/430, 431; 47/44, 58, 48.5

[56] References Cited

U.S. PATENT DOCUMENTS 5,229,288  7/1993  Mori et al. ........................ 435/240.23
5,273,066  12/1993  Graham et al. ........................ 137/78.3

FOREIGN PATENT DOCUMENTS 4 74981  11/1992  Japan .

OTHER PUBLICATIONS

Patterson, D. "Free Volume and Polymer Solubility: A Qualitative View." *Macromolecules* vol. 2, No. 6, Nov.–Dec. 1969: (672–677).

Tanaka, Toyoichi, et al. "Critical Kinetics of Volume Phase Transition of Gels" *Physical Review Letters* vol. 55, No. 22, 25 Nov. 1985: (2455–2458).

Obonai, Y. "Thermo–Responsive Hydro Gel (TRHG) For Tissue Culture of Orchids" *Proceedings of NIOC '96 Nagoya* 1996: (119–122).

Kawanishi, Kazuo et al. "The Sol–Gel Transition and the Liquid–Liquid Phase Separation in Poly(vinyl chloride) Solutions" *Polymer Journal* vol. 18, No. 5, 1986: (411–416).

Heskins, H., and J.E. Guillet. "Solution Properties of Poly-(B–isopropylacrylamide)" *J.Macromol.Sci.–Chem.*, A2(8), Dec., 1968: (1441–1455).

*Primary Examiner*—Toni R. Scheiner
*Attorney, Agent, or Firm*—Leydig, Voit & Mayer, Ltd.

[57] ABSTRACT

A plant is grown or regenerated while suppressing the propagation of bacteria and fungi, by use of a carrier comprising a culture medium and a polymer constituting a network structure wherein the culture medium is substantially absorbed into and retained by the network structure in a proportion of 10% to 100% of the equilibrium culture medium absorption of the polymer constituting the network structure. The propagation of bacteria and fungi is much faster, and the metabolic rate thereof is much larger, than those of a plant. Therefore, the necessity of providing a nutrient (such as water and saccharide) from the culture medium to the bacteria and fungi is much greater than that in the plant tissue. Unlike a liquid medium, the culture medium which has been absorbed in the network structure comprising the polymer is hardly available to the bacteria and fungi, which have high metabolic activity. On the other hand, like a liquid medium, such a culture medium is available to a plant tissue having a low metabolic activity. The propagation of bacteria and fungi is effectively substantially suppressed without affecting the growth or regeneration of the plant.

18 Claims, 5 Drawing Sheets

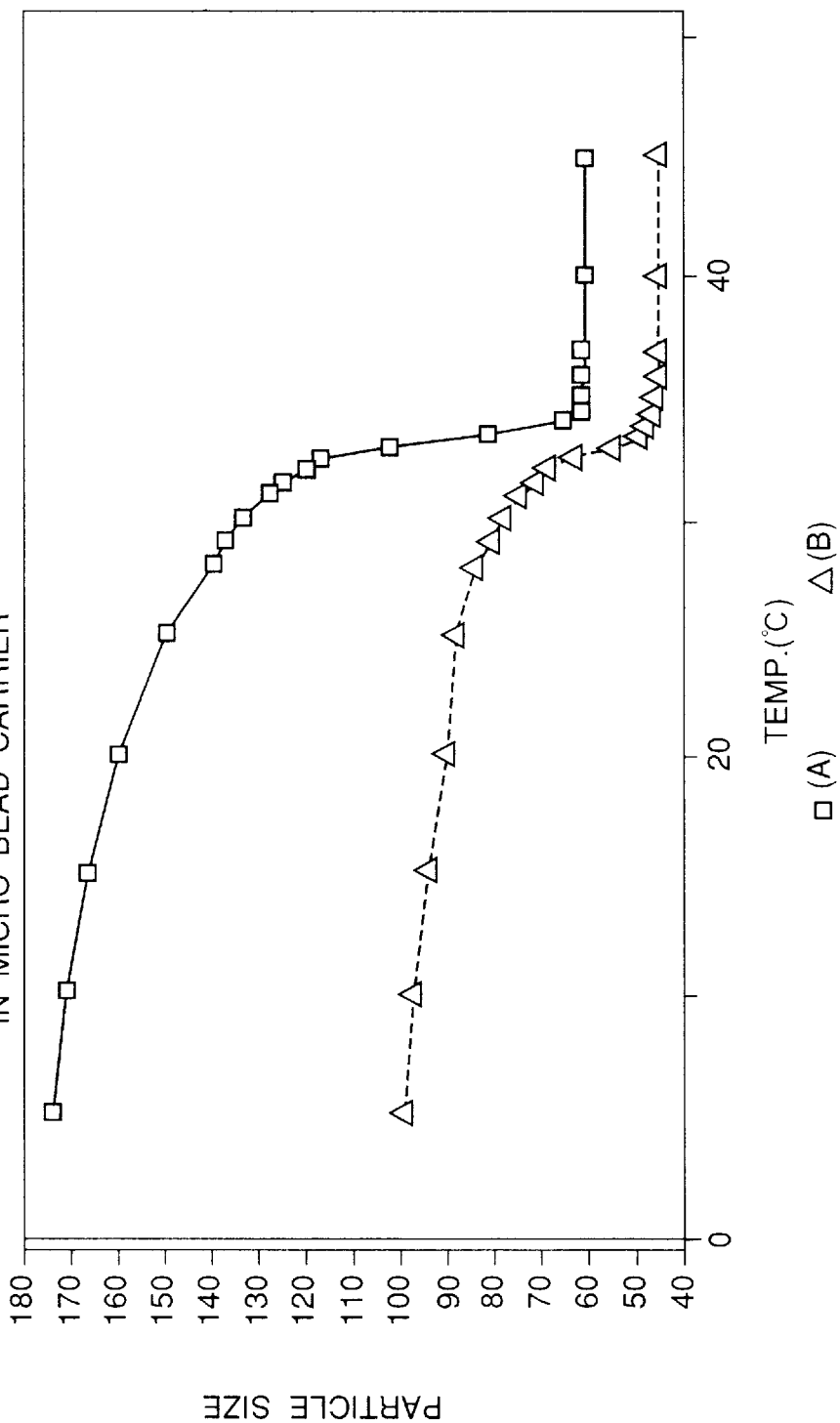

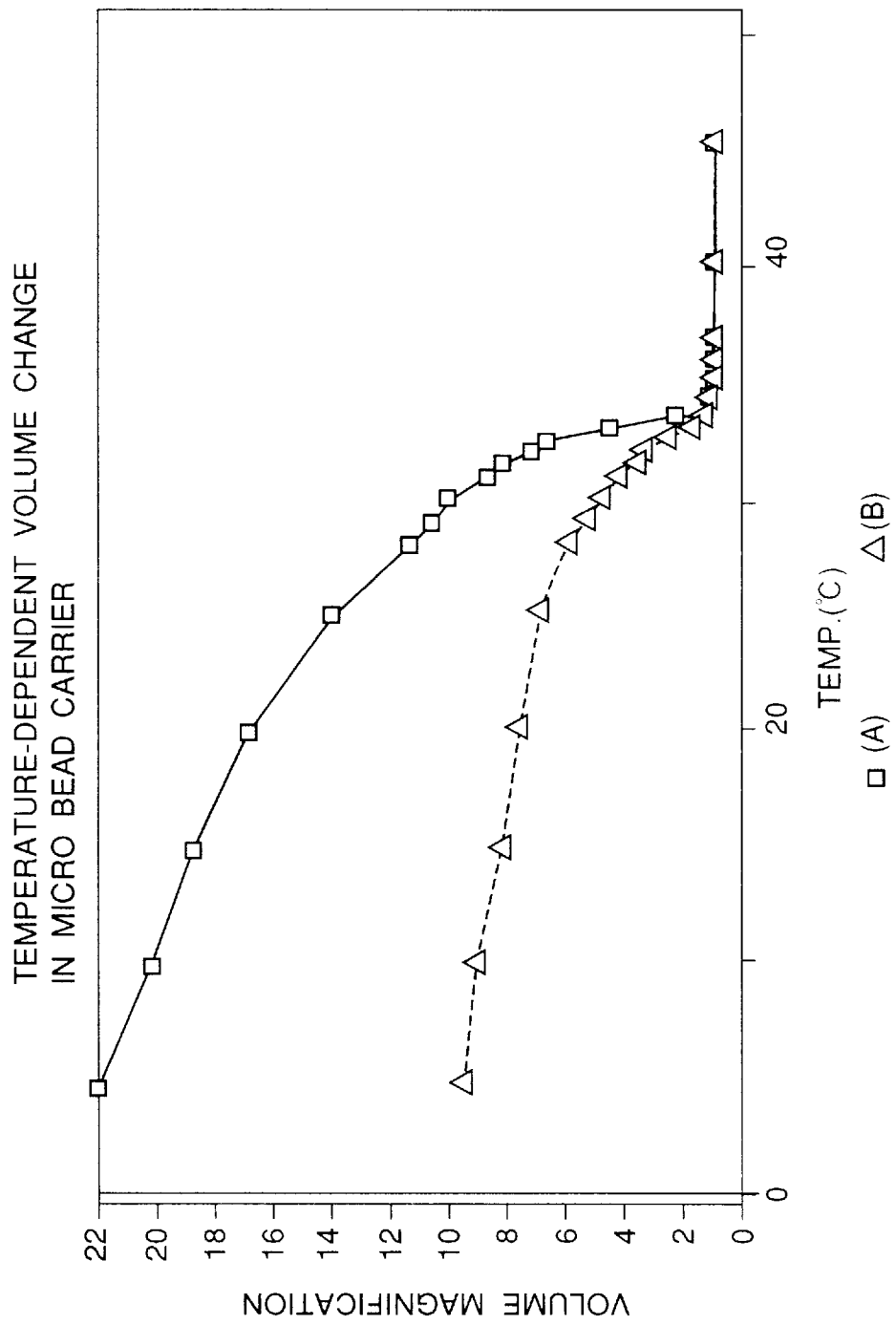

Fig. 3 (Table 1)

| TEMP. °C | (A) PARTICLE SIZE μm | VOLUME V/V0 | (B) PARTICLE SIZE μm | VOLUME V/V0 |
|---|---|---|---|---|
| 5 | 173 | 22.0 | 98 | 9.7 |
| 10 | 170 | 20.6 | 96 | 9.1 |
| 15 | 166 | 19.2 | 93 | 8.3 |
| 20 | 160 | 17.2 | 90 | 7.5 |
| 25 | 150 | 14.2 | 88 | 7.0 |
| 28 | 140 | 11.5 | 84 | 6.0 |
| 29 | 137 | 10.8 | 81 | 5.4 |
| 30 | 134 | 10.1 | 78 | 4.9 |
| 31 | 128 | 8.8 | 75 | 4.3 |
| 31.5 | 125 | 8.2 | 71 | 3.7 |
| 32 | 120 | 7.3 | 69 | 3.4 |
| 32.5 | 117 | 6.7 | 63 | 2.6 |
| 33 | 103 | 4.6 | 55 | 1.7 |
| 33.5 | 82 | 2.3 | 50 | 1.3 |
| 34 | 66 | 1.2 | 48 | 1.1 |
| 34.5 | 62 | 1.0 | 47 | 1.1 |
| 35 | 62 | 1.0 | 46 | 1.0 |
| 36 | 62 | 1.0 | 46 | 1.0 |
| 37 | 62 | 1.0 | 46 | 1.0 |
| 40 | 62 | 1.0 | 46 | 1.0 |
| 45 | 62 | 1.0 | 46 | 1.0 |

Fig. 4 (Table 2)

| KIND OF CARRIER | EQUILIBRIUM WATER ABSORPTION | | |
|---|---|---|---|
| | DISTILLED WATER | PHYSIOLOGICAL SALINE SOLUTION | MS-CULTURE MEDIUM |
| SUMICAGEL S-50 | 600 | 50 | 100 |
| AQUARIC CA-H | 500 | 60 | 100 |

Fig. 5 (Table 3)

| | |
|---|---|
| $KNO_3$ | 672 mg/ℓ |
| $KH_2PO_4$ | 184 mg/ℓ |
| $MgSO_4 \cdot 7H_2O$ | 413 mg/ℓ |
| $Ca(NO_3)_2 \cdot 4H_2O$ | 756 mg/ℓ |
| $NH_4NO_3$ | 108 mg/ℓ |
| $FeNaEDTA$ | 25 mg/ℓ |
| $H_3BO_3$ | 3 mg/ℓ |
| $MnSO_4 \cdot 4 \sim 5H_2O$ | 2 mg/ℓ |
| $ZnSO_4 \cdot 7H_2O$ | 0.22 mg/ℓ |
| $CaSO_4 \cdot 5H_2O$ | 0.05 mg/ℓ |
| $Na_2MoO_4 \cdot 2H_2O$ | 0.05 mg/ℓ |
| $KI$ | 0.83 mg/ℓ |
| $CoCl_2 \cdot 6H_2O$ | 0.02 mg/ℓ |

Fig. 6 (Table 4)

| COMPOSITION OF SUPPORT | FRESH WEIGHT (g) | | |
|---|---|---|---|
| | TOTAL WEIGHT | WEIGHT OF PORTION ABOVE SURFACE | WEIGHT OF PORTION BELOW SURFACE |
| C-PNIPAAm-H | 7.2 | 2.2 | 5.0 |
| C-PNIPAAm-H + Growell MO-2 | 9.2 | 2.4 | 6.8 |
| Growell MO-2 | 7.2 | 1.6 | 5.6 |

SUPPORT FOR GROWING/REGENERATING PLANT AND METHOD OF GROWING/ REGENERATING PLANT

TECHNICAL FIELD

The present invention relates to a support (or carrier) which is suitable for the growth or regeneration of a plant. More specifically, the present invention relates to a method of promoting or accelerating the growth or regeneration of a plant while inhibiting the propagation of bacteria and fungi, by using a support for growing or regenerating the plant which is capable of effectively inhibiting the propagation of bacteria and fungi; and/or a support for growing or regenerating a plant which is capable of easily collecting or transferring (subculturing) the plant; and a method of growing or regenerating a plant by utilizing such a support.

BACKGROUND OF THE INVENTION

In recent years, it has attracted much attention to develop a technique for growing or regenerating a plant having a character suitable for an intended purpose.

Quite recently, on the basis of a technique for growing a plantlet from a growing (or vegetative) point, have been various e.g., those for regenerating a plant from an organ such as leaf, stem, root, petal, and anther (pollen) directly, or by way of a callus or protoplast. Particularly, at the stage of the protoplast, new breeding techniques such as the introduction of a foreign or exogeneous gene using a particle gun and electroporation have been developed, and there have been attempts to grown and regenerate a plant which is more suitable for an intended purpose.

In a case where these new breeding or plant tissue-culturing processes are put to practical use, it is the most important point, commonly in the above techniques, to establish a method of efficiently growing or regenerating a plant which has acquired the above-mentioned intended character.

In view of the physical property of a "culture medium" to be used for the culture process, the plant tissue-culturing processes are roughly classified into a method (liquid culture process) using a liquid culture medium, and a method (solid culture process) using a culture medium which has been converted into a gel state by using agar, gellangum (trade name: GELRITE, e.g., mfd. by San-ei Kagaku Kogyo K.K.), etc.

The liquid culture process in which a plant tissue or cells are grown in a suspension state, may facilitate the rapid and large-quantity multiplication thereof, and therefore such a method is suitable for a bioreactor, etc., which is to be used for the purpose of producing a secondary metabolite of a plant. However, in many cases, the liquid culture process is not suitable for the growth or regeneration of a plant which is intended for the multiplication of a clone. The reason for this is that, in the liquid culture process, a plant is grown in a state such that the plant is soaked in a culture medium, and therefore the resultant plant has an extremely poor resistance to dryness, and it is impossible to transfer the resultant plant into field (or farm) cultivation which is to be conducted at a relatively low humidity.

On the other hand, in the solid culture process using agar gel, etc., the gel state of a culture medium functions as a good support for a plant, and therefore such a method may solve the above-mentioned problem of "soaking in liquid" which will occur in the case of the liquid culture process. Accordingly, the solid culture process has widely been used for growing or regenerating a plant.

However, with respect to the current process (for growing or regenerating a plant (i.e., solid culture process) by using agar, etc., some serious problems as described below have been pointed out.

Thus, in the process for growing or regenerating a plant by using agar, it is extremely difficult to collect (or harvest) the resultant plant, which has been grown or regenerated in the gel-like support such as agar gel, in a state such that the plant is free from the agar gel. Particularly, when some roots are regenerated in the gel-like agar in the step of the formation of roots originating from a shoot, it is extremely difficult to separate such roots from the agar. The agar culture medium to be used for the root-forming step usually contains a saccharide or sugar such as glucose, as a nutrient. Therefore, when the resultant plant having the thus formed roots is as such subjected to cultivation outside a culturing vessel, i.e., in a state such that the agar is attached to the roots, under a non-sterilized condition, the saccharide contained in the agar becomes a cause of the propagation of bacteria. As a result, the resultant efficiency of active root anchoring is markedly decreased, in a case where the root-originating plant is subjected to the cultivation outside the culturing vessel.

At present, there has been adopted a method wherein the agar is mechanically removed from the root-originating plant, and then is washed out with water for the purpose of removing the agar from the plant. However, in such a procedure wherein the agar is mechanically removed, not only are the weak or fragile roots of the root-originating plant to be collected damaged, but also it is difficult to completely remove the minute pieces of the agar gel which have firmly been attached to the roots. As a result, the efficiency of the active root anchoring of the collected plant is inevitably decreased. In addition, the above agar-removing step requires much labor. Such a step becomes a factor of an increase in the production cost.

The above-mentioned problems are based on the physical property of the gel such as agar gel to be used for the conventional solid culture process. More specifically, the agar has a sol-gel transition temperature, and has a property such that it assumes a solution state, namely, a sol state, at a temperature higher than the transition temperature, and it is converted into a gel state at a temperature lower than the transition temperature. Accordingly, the solid culturing process has been practiced, e.g., by using a method wherein an agar gel is formed at a temperature lower than the sol-gel transition temperature, and then a plant is transferred into the resultant agar gel.

However, the melting temperature of the agar gel is very high, i.e., in the neighborhood of 90° C. (Aizo Yamauchi, et al., KOBUNSHI (Polymer) One Point "Functional Gel", page 29, Kyoritsu Shuppan K.K.). Therefore, when a plant, which has been grown or regenerated in the agar culture medium, is intended to be collected in an agar-free state, it is necessary to raise the temperature up to a value higher than the sol-gel transition temperature of agar, so as to convert the agar into a sol state. However, at this time, the plant is exposed to such a high temperature and is seriously damaged. Accordingly, in the conventional solid culture process, it is extremely difficult to collect the plant in an agar-free state by utilizing a temperature change as described above, and therefore the above-mentioned method wherein the agar is mechanically removed has been practiced. However, in the mechanical agar-removing method, some serious problems still remain unsolved, as described above.

In addition, in the course of the solid culture process, a nutrient is supplied to the agar culture medium, and the resultant waste (or egesta) accumulated in the agar culture medium is removed therefrom, both on the basis of the diffusion of the nutrient or waste in the gel. Therefore, the efficiency in the supply of the nutrient and in the removal of the waste is very low, as compared with that in the case of the liquid culture process. Particularly, it is almost impossible in the solid culture process to remove a growth inhibiting substances such as polyphenol produced by the plant per se.

In addition, the collection or recovery of a secondary metabolite of a plant in the agar culture medium is much harder than that in the liquid culture process. More specifically, the reason for this is that the secondary metabolite is seriously damaged inevitably by the high-temperature heating to be employed at the time of dissolving the agar gel containing the secondary metabolite.

On the other hand, the plant (cell) culture processes for the purpose of growing or regenerating a plant may generally be classified into a saccharide-involving (or saccharide-relating) culture process and a saccharide-free culture process, in view of the supply of a nutrient.

In the saccharide-involving culture process, a saccharide such as sucrose, glucose, and fructose is added into the culture medium (or support) as a nutrient, and therefore the saccharide-involving culture process is suitable for the culture of a plant at a stage at which the leaf thereof capable of photo-synthesis is still small, i.e., a young plant. On the other hand, the saccharide-free culture process is suitable for the culture of a plant at a stage at which the leaf thereof capable of photo-synthesis becomes large, i.e., a grown plant. In the saccharide-free culture process, in general, the plant is supplied with carbon dioxide and is irradiated with light so as to promote the photo-synthesis reaction.

In the above-mentioned saccharide-involving culture process, since the saccharide contained in the culture medium increasingly promotes the propagation of bacteria and fungi, the contamination of the culture medium with various germs will provide fatal results. Accordingly, the saccharide-involving culture process has heretofore been conducted under a strictly sterilized environment.

On the other hand, in the saccharide-free culture process, the propagation of bacteria and fungi is relatively slow as compared with that in the saccharide-involving culture process. However, even in the case of the saccharide-free culture process, the contamination of culture medium may possibly provide fatal results similarly as in the case of the saccharide-involving culture process. From such a viewpoint, in practice, the saccharide-free culture has heretofore been conducted under a sterilized or closed environment.

In the above-mentioned sterilized culture process wherein the contamination with bacteria must be minimized, there have been posed serious problems such that a costly apparatus is required in order to provide the sterilized environment; operations for sterilization or disinfection of various devices, a culture medium, etc., to be required for the procedure are extremely complicated and troublesome; and most of the operations per se for the transferring of a plant, etc., themselves depend on human labor and the saving of the labor in these operations is difficult.

Further, in the solid culture process using an agar gel, along with progress in the growth or regeneration of a plant, an organ (such as root) of the resultant plant tissue generally destroys the agar gel so as to provide voids between the agar gel and the plant (in some cases, these voids are filled with a liquid culture medium), when such an organ of the plant tissue is grown and penetrated into the agar gel functioning as the support for the plant. The cause for this phenomenon is considered to be that the agar gel has a crosslinked network structure in the interior thereof, but the growing or regenerating plant cannot penetrate into the network crosslinking structure, and therefore the plant inevitably destroys the agar gel so that the plant tissue is grown in the culture medium. Based on the property of the agar gel, the voids which have been provided between the plant tissue and the agar gel cannot be filled with the agar, unless the agar gel is again converted into a sol state. However, the melting temperature of the agar gel is as high as about 90° C., and therefore it is practically impossible to convert the agar gel into a sol state so as to fill the above-mentioned voids in the agar (in consideration of the prevention of the thermal damage to the plant tissue).

In addition, the agar gel, once formed, has a characteristic such that it does not absorb a further amount of the culture medium even if the culture medium is newly added to the agar gel. In combination with such an additional characteristic of the agar gel, it is impossible to fill the above-mentioned voids which have been formed between the plant and the agar gel, and further the culture medium occupying the voids is not absorbed into the gel. In other words, even in the solid culture process using the agar gel, the environment surrounding the plant tissue is equivalent to that in the liquid culture process under microscopic observation. In addition, it has been pointed out that the agar gel has a serious problem such that it may cause a syneresis phenomenon wherein the culture medium is separated from the agar gel, and bacteria and fungi are rapidly propagated through the culture medium which has been separated from the gel.

Accordingly, even the agar gel culture process has a serious problem such that once the culture medium is contaminated, bacteria and fungi cannot penetrate into the interior of the agar gel, but the bacteria and fungi are extremely rapidly propagated through the voids which have been provided between the plant and the agar gel, or through the culture medium which has been separated from the agar gel.

An object of the present invention is to provide a support (or carrier) for growing or regenerating a plant which promotes the growth of the plant while effectively suppressing the propagation of bacteria and fungi; and a process for growing or regenerating a plant which enables the saving of labor by using such a support.

Another object of the present invention is to provide a support (or carrier) for growing or regenerating a plant which can easily collect or transfer the grown or regenerated plant without damaging the plant; and a process for growing or regenerating a plant by using such a support.

A further object of the present invention is to provide a support (or carrier) for growing or regenerating a plant, from which a saccharide such as glucose, which is a nutrient for bacteria and fungi, may be removed to the outside of the plant-growing/regenerating system, when the plant which has been grown or regenerated under a sterilized environment is transferred into a non-sterilized environment such as field or farm; and a process for growing or regenerating a plant by using such a support.

DISCLOSURE OF INVENTION

As a result of earnest study, the present inventor has found that it is extremely effective in solving the above-mentioned problems by using hydrogel particles having a predetermined size in a dried state thereof and also having a crosslinked structure, as a support for growing or regenerating a plant.

The support for growing or regenerating a plant according to the present invention is based on the above discovery and comprises: particles having a dimension in the range of 0.1 μm to 1 cm in a dried state, and comprising a hydrogel having a crosslinked structure (Hereinbelow, the support in such an embodiment is sometimes referred to as "support according to first embodiment").

The present invention also provides a support for growing or regenerating a plant, wherein a grown or regenerated tissue of the plant does not penetrate into the interior of the hydrogel particle having a crosslinked structure.

The present invention further provides a support for growing or regenerating a plant, wherein the hydrogel particles are in the form of: micro-beads, fibers, flakes, a sponge, a film or a plate (indeterminate shape).

The present invention further provides a method of growing or regenerating a plant, wherein a support is swollen with a culture medium in a culturing vessel so as to reduce the fluidity of the culture medium to be formed into a gel state, and to support a plant by the gel, thereby to grow or regenerate the plant; the support comprising particles having a dimension in the range of 0.1 μm to 1 cm in a dried state, and comprising a hydrogel having a crosslinked structure.

The present invention further provides a method of growing or regenerating a plant, wherein the plant is grown or regenerated by using the support, and thereafter an excess of water is added to the support to increase the fluidity of the support, thereby to recover the plant.

The above-mentioned support according to the first embodiment is one utilizing a property of the hydrogel particles having a size in the range of 0.1 μm to 1 cm in a dried state and having a crosslinked structure are swollen in water or a culture medium so that their volume is reversibly increased. Herein, the term "hydrogel" refers to a gel comprising, at least, a crosslinked water-soluble or hydrophilic polymer, and water as a dispersion liquid (or a liquid comprising water as a main component) supported by the polymer.

The above-mentioned support according to the present invention is one obtained by crosslinking a water-soluble or hydrophilic polymer so that when the resultant polymer is placed in a solution, it absorbs water to be swollen, but is not dissolved therein. The degree of the swelling of such a support may be changed by changing the kind of the water-soluble or hydrophilic polymer, and/or the degree of the crosslinking thereof, etc. In the present invention, it is preferred to regulate the above degree of crosslinking so that the grown or regenerated tissue of a plant cannot penetrate into the inside of the crosslinked network structure of the hydrogel particle according to the present invention, but the tissue is propagated along the clearances between the above hydrogel particles. The ability of the support according to the present invention for supporting a plant in the course of the growth or regeneration thereof can be regulated by the above-mentioned degree of swelling, the volume ratio between the above support and culture medium in a culture vessel (culture system), the shape and dimension of the above support, etc.

On the other hand, when the plant which has been grown or regenerated by using the above support is collected (or harvested) from the support, for example, it is easy to separate the plant from the support by adding an excess of water or a culture medium into the culture vessel so as to dilute the support contained in the culture vessel (i.e., to decrease the volume ratio of the support to the culture medium) and to decrease the plant-supporting ability of the support.

As a result of further study of the present inventor, it has also been found that the above-mentioned problems encountered in the prior art are solved extremely effectively by using a polymer which is capable of reversibly converting between a liquid state and a gel state (i.e., a temperature-responsive polymer having a LCST (lower critical solution temperature)) as a support for growing and/or regenerating a plant.

The support for growing or regenerating a plant according to the present invention is based on the above discovery and comprises: a polymer which has been obtained by crosslinking a temperature-responsive polymer having a LCST (lower critical solution temperature). (Hereinafter, the support according to such an embodiment is sometimes referred to as "support according the second embodiment".) With respect to the details of the above "LCST", e.g., a paper of D. Patterson; Macromolecules, 2, 1672 (1969) may be referred to.

The present invention further provides a method of growing or regenerating a plant, comprising:
dispersing a carrier for growing or regenerating a plant, which has been obtained by crosslinking a temperature-responsive polymer having a LCST (lower critical solution temperature), in a predetermined culture medium at a temperature higher than the LCST;
mixing a plant in the resultant dispersion; and
lowering the temperature to a value lower than the LCST to reduce the fluidity of the dispersion and to convert the dispersion into a gel state, thereby to grow or regenerate the plant.

The present invention also provides a method of growing or regenerating a plant, comprising:
dispersing a carrier for growing or regenerating a plant, which has been obtained by crosslinking a temperature-responsive polymer having a LCST (lower critical solution temperature), in a predetermined culture medium at a temperature higher than the LCST;
lowering the temperature to a value lower than the LCST to reduce the fluidity of the resultant dispersion and to convert the dispersion into a gel state; and
disposing or inserting a plant on or in the gel, thereby to grow or regenerate the plant.

The above support according to the second embodiment is one which utilizes a property such that a polymer obtained by crosslinking a temperature-responsive polymer having a LCST absorbs water at a temperature lower than the LCST in water or a culture medium so as to be swollen, and also releases the water at a temperature higher than the LCST to be shrunk so as to markedly change the volume thereof.

Accordingly, both of a gel state having an extremely low flowability at a temperature lower than the LCST, and a liquid state having an extremely high flowability at a temperature higher than the LCST may be realized, e.g., by controlling the quantitative ratio of the support and the culture medium in the culture medium dispersion of the carrier according to the present invention, the degree of crosslinking of the temperature-responsive polymer, the dimension of the support, etc. Such a conversion between the liquid state and the gel state is reversible with respect to temperature. Further, the temperature for causing the conversion between the liquid state and the gel state may be determined by the above LCST.

As a result of further study of the present inventor, it has been found that the use of a carrier obtained by causing a culture medium to be substantially absorbed and retained in the network structure of a polymer (e.g., in the network structure constituting the above-mentioned "first support" and/or "second support") enables the growth or regeneration of a plant while remarkably suppressing the propagation of bacteria, fungi, etc., thereby to provide a further effect on the achievement of the above-mentioned objects.

The support for growing or regenerating a plant is based on the above discovery and comprises: a culture medium and a polymer, wherein the culture medium is substantially absorbed into and retained by the network structure comprising the polymer.

In the above-mentioned carrier, it is preferred that the above network structure constitutes a hydrogel having a crosslinked network structure which inhibits the penetration thereinto of bacteria, fungi, and/or regenerated tissue of the plant.

Further, in the above support, the network structure material in a dried state has a dimension in the range of 0.1 $\mu$m to 1 cm, and has a carrier shape of either of micro-beads, fibers, film, or indeterminate shape.

The present invention further provides a method of growing or regenerating a plant, wherein a carrier comprising a culture medium and a polymer constituting a network structure is used so as to grow or regenerate a plant while suppressing: the propagation of bacteria and fungi; the culture medium being substantially absorbed into and retained by the network structure in a proportion of 10% to 100% of the equilibrium culture medium absorption of the polymer constituting the network structure.

In the above support according to the present invention, in general, the network structure comprising the above polymer has an ability to absorb a culture medium so as to form a hydrogel. In other words, the carrier according to the present invention generally assumes a hydrogel state.

In the carrier according to the present invention, it is preferred to use a polymer which has been obtained by crosslinking a water-soluble or hydrophilic polymer compound, as the polymer constituting the network structure. This type of the polymer has a property such that it absorbs water to be swollen in an aqueous solution, but is not to dissolved therein. The equilibrium culture medium absorption (amount) as described hereinafter-can be changed by changing the kind of the above-mentioned water-soluble or hydrophilic polymer, and/or the degree of crosslinking.

When the above-mentioned support according to the first embodiment of the present invention is used as the above polymer constituting the network structure, it is possible to effectively utilize the property of the hydrogel particles having a crosslinked structure and having a dimension, in a dried state, in the range of 0.1 $\mu$m to 1 cm, that they are swollen in water or a culture medium so as to reversibly increase the volume thereof.

When a culture medium is completely absorbed into the above "support according to the first embodiment" so as to constitute the carrier according to the present invention, the resultant "a state at which the culture medium is completely absorbed" is usually a semi-solid gel state. Therefore, the resultant carrier may preferably be used as a support for culturing a plant. In addition, it is also possible to easily supplement such a gel with water, a nutrient, etc., which have become insufficient in the culturing process, as an additional (or supplemental) fertilizer.

In addition, the plant which has been grown or regenerated by using the carrier according to such an embodiment of the present invention may easily be collected or transferred, e.g., by adding an excess of water or a culture medium to the carrier in the gel state so as to convert the gel into a sol state without damaging the resultant regenerated tissue.

On the other hand, when the above "support according to the second embodiment" is used as the above polymer constituting the network structure, it is possible to effectively utilize a property of the polymer comprising a crosslinked temperature-responsive polymer having a LCST, such that it absorbs water in water or a culture medium at a temperature lower than the LCST to be swollen; and it releases water to be shrunk at a temperature higher than the LCST, thereby to markedly change the volume thereof.

When the hydrogel particles comprising the crosslinked temperature-responsive polymer are used as the support according to present invention, it is possible to easily remove a nutrient such as glucose required for the propagation of bacteria and fungi, from the interior of the carrier only by using a temperature change, thereby suppressing the bacteria and fungi more effectively. Further, it is also possible that the culturing waste accumulated in the carrier is removed only by utilizing the above temperature change, and the carrier is then absorbs a fresh culture medium and the resultant carrier is used for the culture process; or the resultant carrier is used after the transfer to farm cultivation. Further, the conversion between the liquid state and the gel state can be performed by utilizing a temperature change, and therefore it is possible to transfer or collect the grown or regenerated plant substantially without damaging the plant.

According to the investigations of the present inventor, the reason for the above phenomenon, that the propagation of bacteria and fungi is effectively suppressed by using the support or carrier according to the present invention, is presumed to be that the propagation of bacteria and fungi is much faster, and the metabolic rate thereof is much larger, than those of a plant, therefore the necessity of the supplement or delivery of a nutrient (such as water and saccharide) from the culture medium to the bacteria and fungi is much greater than that in the plant tissue.

More specifically, according to the investigations of the present inventor, it is in the carrier according to the present invention having the above-mentioned structure, the culture medium which has been absorbed in the network structure comprising the polymer is hardly available to the bacteria and fungi having a high metabolic activity, unlike a usual liquid medium, on the other hand such a culture medium is available to a plant tissue having a low metabolic activity, substantially equally in the case of the usual liquid medium, whereby the propagation of bacteria and fungi is effectively and substantially suppressed without affecting the growth or regeneration of the plant.

The above-mentioned support or carrier according to the present invention may be used under a sterilized condition (e.g., in a sterilized culture vessel), and may also be used under a non-sterilized condition as described hereinafter. The "culture under a non-sterilized condition" refers to a culture or cultivation process in an open system other than a culture process in a sterilized closed system. Specific examples of the "cultivation or culture under a non-sterilized condition" includes, e.g., cultivation in an open-air system such as greenhouse, vinyl house, field and farm, and culture in a vessel under a non-sterilized condition.

Under a non-sterilized environment, it is possible to use the support or carrier according to the present invention in combination with another support or carrier (such as soil) as desired. In other words, it is possible to use the support or carrier according to the present invention in a mixture with "another support or carrier". Further, at the time of transfer or repotting, etc., it is also possible that a plant carrying the support or carrier according to the present invention attached thereto is transferred to the culture or cultivation thereof using "another support or carrier" under a non-sterilized condition.

At the time of such transfer of a plant from a sterilized condition to a non-sterilized condition, as described in Examples appearing hereinafter, the support or carrier per se, and/or a culture medium or nutrient (such as saccharide) may be removed from the plant as desired, and thereafter the resultant plant is transferred to the non-sterilized condition. If a factor capable of inhibiting the culture or cultivation under the non-sterilized condition (such as saccharide and culture medium to be used under the sterilized condition) can be removed, the removal of the carrier or support per se from the plant is omissible. That is, the resultant plant may be transferred to another carrier such as soil, while the carrier or support is left being attached to the root, etc., of the plant.

Regardless of the sterilized or non-sterilized condition, when the support or carrier according to the present invention (especially, support or carrier comprising a polymer having a LCST) is used as at least a part of a support or carrier for growing a plant, the support or carrier may further contain another substance other than the culture liquid medium (such as natural organic and inorganic substance) mixed therein. When "another substance" is mixed in the support or carrier, the possibility of propagation of various germs tends to be somewhat higher because of the presence of voids or carbon sources, but on the basis of the feature of the support or carrier according to the present invention, it is possible to supplement a nutrient or fertilizer, the removal of a culturing waste including used or old culture medium, etc., without damaging the plant. Accordingly, even when the carrier or support contains "another substance" mixed therein, the use of the support or carrier according to the present invention is effective for the growth of a plant.

BRIEF DESCRIPTION OF DRAWINGS

FIG. 1 is a graph showing an example of the temperature-dependent particle size change in the micro-bead type carrier according to the present invention.

FIG. 2 is a graph showing an example of the temperature-dependent volume change of a micro-bead type carrier according to the present invention.

FIG. 3 (Table 1) is a table showing the data corresponding to the above FIGS. 1 and 2.

FIG. 4 (Table 2) is a table showing the equilibrium water absorption data of a polymer support used in Example appearing hereinafter.

FIG. 5 (Table 3) is a table showing the composition of a liquid medium used in Example appearing hereinafter.

FIG. 6 (Table 4) is a table showing the results of the growth obtained under a non-sterilized condition in Example appearing hereinafter.

DETAILED DESCRIPTION

Hereinbelow, the present invention will be described in detail with reference to the accompanying drawings, as desired.
(Equilibrium culture medium absorption)

In the carrier according to the present invention, it is preferred that a culture medium is absorbed into and retained in the network structure comprising a polymer, in a proportion of 10%–100% of the equilibrium culture medium absorption. Herein, the "equilibrium culture medium absorption $(E_a)$" is defined as the weight of a culture medium which has been absorbed into a polymer to be used for the carrier according to the present invention, when the polymer (in a dried state, weight $W_p$=1 g) is immersed in a large excess of the culture medium (culture medium to be used for the carrier according to the present invention) at a predetermined temperature (about 25° C.) for at least 3 days, until the swelling of the polymer reaches an equilibrium. With respect to this "equilibrium of swelling", e.g., a paper of T. Tanaka, et al., Phys. Rev. Lett., 55, 2455 (1985) may be referred to.

More specifically, when the total weight of (polymer)+(culture medium absorbed by polymer) after the swelling of the polymer reaches an equilibrium is represented by $W_e$, the equilibrium culture medium absorption $(E_a)=W_e-W_p$.

In the present invention, the state at which the polymer has completely absorbed the culture medium is a state such that the ratio (M/G) of the weight of the polymer (G) to the weight of the culture medium (M) is not larger than the equilibrium culture medium absorption $E_a$.

Accordingly, in view of the suppression of the propagation of bacteria and fungi in the carrier according to the present invention, it is preferred that the above M/G ratio is not larger than the equilibrium culture medium absorption $E_a$ of the polymer (i.e., $M/G \leq E_a$). As the above M/G ratio becomes smaller, the effect of the suppression of the propagation of the bacteria and fungi is enhanced. However, when the M/G ratio becomes too small, it is possible that the ability of the carrier to absorb the culture medium exceeds the ability of the plant tissue to absorb the culture medium, whereby the supplement of the nutrient such as water to the plant tissue possibly becomes difficult.

From such a viewpoint, there is a region wherein the M/G ratio has a preferred value. Such a "preferred region" can be different depending on the kind of a plant to be grown, or the kind of the bacteria or Fungi to be prevented, but in general, the M/G ratio in the carrier according to the present invention may preferably be 10%–100%, more preferably 20%–60% of the equilibrium culture medium absorption $E_a$ of the polymer constituting the carrier.

As described above, the conventional liquid culture process or culture process using an agar gel (a culture medium, etc., is present even in voids provided between the plant and the agar gel, and therefore such a culture process is equivalent to the liquid culture process microscopically or substantially) provides an environment which can be a hotbed for the propagation of bacteria and fungi. On the contrary, when the carrier according to the present invention is used, the liquid medium is not substantially present in the carrier, and therefore the propagation of bacteria and fungi is effectively suppressed.
(Shape of carrier)

The shape or form of the carrier according to the present invention is not particularly limited, but may appropriately be selected depending on the kind or dimension of a plant to be grown or regenerated. Specific examples of the shape of the carrier may include various shapes such as particles, micro-beads, fibers, flakes, sponge-like shape, film-like shape, and sheet-like (indeterminate) shape.

The dimension of the network structure material in a dried state comprising a polymer constituting the carrier according to the present invention can appropriately be selected depending on the kind or size of plant tissue to be grown or regenerated, etc., dimension may generally be in the range of 0.1 µm to 1 cm, more preferably in the range of 1 µm to 1 mm.

In the carrier according to the present invention, the above-mentioned "dimension in a dried state" refers to the average of maximum diameters (maximum dimensions) of the particles of the network structure material constituting the carrier (average of values obtained by measuring at least 10 particles). More specifically, for example, the following size may be treated as the "dimension in a dried state" in accordance with the shape of the above particles.

Micro-bead shape: particle size (average particle size)

Fiber shape: average of lengths of respective fiber pieces

Film shape, indeterminate shape: average of maximum dimensions of respective pieces In the present invention, in place of the above "average of maximum values", it is also possible to use the diameter of a "ball" having a volume equal to the average of the volumes of respective pieces (average of values obtained by measuring at least 10 pieces) as the "dimension in a dried state" of the particles of the above network structure material.

In an embodiment wherein the carrier according to the present invention is shaped into the above particle form, when the regenerated plant tissue penetrates into the carrier which has absorbed a culture medium, the regenerated plant tissue can penetrate into the carrier so as to be grown along gaps or clearances between the carrier particles, without destroying the gel, unlike in the case of the conventional agar gel.

Further, the culture medium in a liquid state is not present in the voids between the carrier particles which have been provided by the regenerated tissue having been grown and penetrated into the carrier particles, as described hereinabove, and the carrier particle which has absorbed the culture medium generally becomes a very flexible hydrogel, whereby the voids may be mechanically filled with the hydrogel.

As described above, when a carrier in a particle form is used, unlike in the case of the conventional agar gel, etc., the space which has been formed due to the penetration of the regenerated tissue of a plant into the carrier is promptly sealed, but also the liquid culture medium capable of being a hotbed of the propagation of bacteria and fungi is also absorbed into the interior of the carrier. Accordingly, even when bacteria and fungi are temporarily attached to the surface of the carrier, unlike in the case of using the conventional agar gel, there is no problem such that bacteria and fungi penetrate into the gel to be propagated through the voids which have been formed between the regenerated tissue and the agar gel.

Hereinbelow, there will be explained in detail the respective components constituting the support or carrier according to the present invention.

(Culture medium)

In the present invention, as the culture medium or culturing liquid to be used in combination with the above-mentioned polymer, it is possible to use a known culture medium or culturing liquid (for growing and/or regenerating a plant) containing substantially no agar such as a Murashige-Skoog culture medium (MS-Culture Medium) without particular limitation.

(Water-soluble or hydrophilic polymer)

Specific examples of the water-soluble or hydrophilic polymer constituting a network structure or hydrogel constituting the carrier according to the present invention may include: methyl cellulose, dextran, polyethylene oxide, polypropylene oxide, polyvinyl alcohol, poly N-vinyl pyrrolidone, polyvinyl pyridine, polyacrylamide, poly-N-methyl acrylamide, poly-N-isopropyl acrylamide, poly-N,N-diethyl acrylamide, poly-N-cyclopropyl acrylamide, poly-N-acryloyl pyrrolidine, poly-N,N-ethyl methyl acrylamide, poly-N-ethyl acrylamide, polymethacrylamide, poly-N-n-propyl methacrylamide, poly-N-isopropyl methacrylamide, poly-N-cyclopropyl methacrylamide, polyhydroxyethyl acrylate, polyhydroxymethyl acrylate, polyacrylic acid, polymethacrylic acid, polyvinylsulfonic acid, polystyrenesulfonic acid and their salts, poly-N,N-dimethylaminoethyl methacrylate, poly-N,N-diethyl aminoethyl methacrylate, poly-N,N-dimethylaminopropyl acrylamide, and their salts, etc.

(Crosslinked structure)

As a method of imparting a crosslinked structure to the above polymer, there are a method of introducing a crosslinked structure at the time of the polymerization of a monomer; and a method of introducing a crosslinked structure after the completion of polymerization of a monomer. In the present invention, either of these methods may be adopted.

The former method may preferably be conducted by copolymerizing a monomer for providing the above water-soluble or hydrophilic polymer, and a bifunctional monomer (or multi-functional monomer having at least two functional groups). Specific examples of such a bifunctional monomer may include: N,N-methylenebis-acrylamide, hydroxyethyl dimethacrylate, divinylbenzene, etc.

In the latter method, it is typical form a crosslink between molecules by utilizing the energy such as light, electron beam, and $\gamma$-ray irradiation.

Alternatively, the latter method can also be conducted by crosslinking the above water-soluble or hydrophilic polymer by using, as a crosslinking agent, a multi-functional molecule having therein a plurality of functional groups (such as isocyanate group) which is capable of being bonded to a functional group (such as amino group) of the above water-soluble or hydrophilic polymer.

In the present invention, the above-mentioned "equilibrium culture medium absorption" of a polymer for providing the network structure is dependent on the crosslinked structure, crosslinking density (or density of crosslinking) of the polymer. As the crosslinking density becomes lower, the equilibrium culture medium absorption is increased. In the former method (wherein the crosslinked structure is introduced at the time of the polymerization of a monomer), the crosslinking density can arbitrarily be controlled, e.g., by changing the copolymerization ratio of the bifunctional monomer. In the latter method (wherein the crosslinked structure is introduced after the completion of the polymerization of a monomer), the crosslinking density can arbitrarily be controlled, e.g., by changing the quantity of irradiation such as light, electron beam, and $\gamma$-ray.

In the present invention, the crosslinking density may preferably be in the range of 0.2 mol % to 10 mol %, more preferably 0.5 mol % to 4 mol %, in terms of the ratio of the moles of the branching point to the moles of all the monomer. Alternatively, when the crosslinked structure is introduced by the former method, the crosslinking density may preferably be in the range of 0.3 wt % to 3 wt %, more preferably 0.5 wt % to 2 wt %, in terms of the copolymerization weight ratio of the bifunctional monomer to all the monomers (inclusive of the bifunctional monomer per se).

When the crosslinking density exceeds the above-mentioned range thereof, the culture medium-absorbing ability of the carrier according to the present invention is reduced, the effect of the carrier for suppressing the propagation of bacteria and fungi is reduced, and simultaneously the amount of the culture medium contained in the carrier is reduced and the ability thereof for supplementing a nutrient such as water to a plant is also reduced. On the other hand, when the crosslinking density is below the above-mentioned range, the network structure of the hydrogel becomes sparse, bacteria, Fungi or regenerated tissue is more liable to penetrate into the gel, and simultaneously the gel becomes mechanically weak, and is less able to function as a support for culturing a plant.

The crosslinking density (molar ratio of the branching points with respect to all the monomer) may be determined, e.g., by $^{13}$C-NMR (nuclear magnetic resonance absorption) measurement, IR (infrared absorption spectrum) measurement, or elemental analysis.

(Shaping method)

As the method of shaping of the carrier according to the present invention, it is possible to use an ordinary method of shaping a polymer.

When the simplest method is used, a monomer for providing the water-soluble or hydrophilic polymer, the above-mentioned bifunctional monomer, and a polymerization initiator are dissolved in water, and subjected to polymerization by use of heat or light, whereby a hydrogel can be prepared. The resultant hydrogel is mechanically crushed or pulverized, the unreacted monomer, the remaining polymerization initiator, etc., are removed therefrom by washing with water, and thereafter the resultant product is dried, thereby to provide a carrier according to the present invention.

Further, when the monomer for providing the water-soluble or hydrophilic polymer is liquid, the bifunctional monomer and polymerization initiator are added into the monomer, the resultant mixture is polymerized by bulk polymerization by use of heat or light, the resultant product is mechanically crushed, the unreacted monomer and the remaining bifunctional monomer are removed therefrom by extraction with water, and the product is dried, whereby a carrier according to the present invention can be provided.

On the other hand, when the carrier according to the present invention in a micro-bead form is intended to be prepared, it is possible to use an emulsion polymerization method, a suspension polymerization method, a precipitation polymerization method, etc. Particularly, a reverse-phase suspension polymerization method may preferably be used. In the reverse-phase suspension polymerization method, as a dispersion medium, an organic solvent which doesn't dissolve the monomer and the resultant polymer is preferred. For example, a saturated hydrocarbon such as hexane is preferred. In addition, it is also possible to use a surfactant (e.g., a nonionic surfactant such as sorbitan fatty acid ester) as a suspension auxiliary in combination with the above organic solvent.

The particle size of the resultant micro-bead can be controlled by the kind or amount of the surfactant to be added, the stirring speed, etc. As the polymerization initiator, either of a water-soluble polymerization initiator, and a water-insoluble polymerization initiator can be used.

When the carrier according to the present invention is formed into a fiber shape, film shape, etc., for example, it is possible to use a method wherein an aqueous solution of a water-soluble polymer is extruded into an organic solvent which is unmixable with water by using a die, etc., to form each of the predetermined shapes, then the resultant product is irradiated with light, electron beam, γ-ray, etc., so as to impart a crosslinked structure to the polymer. Further, it is also possible to use a method wherein the above water-soluble polymer is dissolved in an organic solvent or water, is shaped by a solvent casting method, and then is irradiated with light, electron beam, γ-ray, etc., so as to impart a crosslinked structure to the polymer.

Further, it is also possible to mechanically crush either of the resultant shaped products having various shapes obtained by the above methods so as to shape the product into a support having a desired dimension.

(Liquid-gel transition temperature)

In the present invention, the terms "liquid state" "gel state" and "liquid-gel transition temperature" are defined in the following manner. With respect to these definitions, a paper (Polymer Journal, 18(5), 411–416 (1986)) may be referred to.

Thus, 1 mL of a dispersion (liquid) of a support is poured into a test tube having an inside diameter of 1 cm, and is left standing for 12 hours in a water bath which is controlled at a predetermined (constant) temperature. Thereafter, in a case where the interface (meniscus) between the dispersion of the support and air is deformed (inclusive a case wherein the dispersion of the support flows out from the test tube) due to the weight of the dispersion of the support per se when the test tube is turned upside down, the above dispersion of the support is defined as a "liquid state" at the above-mentioned predetermined temperature.

On the other hand, in a case where the interface (meniscus) between the dispersion of the support and air is not deformed due to the weight of the dispersion of the support per se even when the test tube is turned upside down, the above dispersion of the support is defined as a "gel state" at the above-mentioned predetermined temperature.

On the other hand, when the temperature at which the "gel state" is converted into the "liquid state" is determined while gradually increasing the above "predetermined temperature" (e.g., in 1° C. increment), the thus determined transition temperature is defined as a "liquid-gel transition temperature". At this time, alternatively, it is also possible to determine the above temperature at which the "liquid state" is converted into the "gel state" while gradually decreasing the "predetermined temperature" (e.g., in 1° C. decrement).

In the present invention, the above liquid-gel transition temperature may preferably be higher than 0° C. and not higher than 60° C., more preferably, not lower than 4° C. and not higher than 50° C. (particularly preferably, not lower than 4° C. and not higher than 40° C.), in view of the prevention of thermal damage to a plant. The polymer having such a preferred liquid-gel transition temperature may easily be selected from specific compounds as described below, according to the above-mentioned screening method (method of measuring the liquid-gel transition temperature).

In the process for growing or regenerating a plant according to the present invention, it is preferred to set the above-mentioned liquid-gel transition temperature (a °C.) between the temperature at which the plant is grown or regenerated (b °C.), and the temperature at which the grown or regenerated plant is collected or transferred (c °C.). In other words, the above-mentioned three kinds of temperatures of a °C., b °C. and c °C. may preferably have a relationship of b<a<c. More specifically, the value of (a–b) may preferably be 1°–40° C., more preferably 2°–30° C. On the other hand, the value of (c–a) may preferably be 1°–40° C., more preferably 2°–30° C.

The temperature-responsive polymer having a LCST to be used in the present invention has a property such that the polymer is insoluble in water or a culture medium at a temperature higher than the LCST, but is converted into a soluble state at a temperature lower than the LCST.

It is considered that the state change of the temperature-responsive polymer is based on the hydration and dehydration phenomena. With respect to such phenomena, Haskins, M., et al.; *J. Macromol. Sci. Chem.*, A2(8), 1441, 1968, provides a description thereof by using poly-N-isopropyl acrylamide (PNIPAAm) as an example of such polymers. The PNIPAAm is a polymer having a negative solubility-temperature coefficient with respect to water. At a lower temperature, there is formed a hydrate (oxonium hydroxide) depending on the hydrogen bonding between the PNIPAAm molecule and the water molecule. However, it is considered that the hydrate is decomposed by increasing the temperature up to a value higher than the LCST to be dehydrated, and as a result, PNIPAAm molecules are aggregated with each other to be precipitated.

When a crosslinked structure is imparted to the above temperature-responsive polymer having a LCST, the resultant polymer is not dissolved but can retain a swollen gel state even in water or a culture medium at a temperature lower than the LCST. On the other hand, when the temperature is raised to a value higher than the LCST, the polymer is converted into a water-soluble state, whereby water is separated from the gel and the volume of the crosslinked material is markedly decreased. As described above, the support for growing or regenerating a plant and the method for growing or regenerating a plant according to the present invention utilize such a property of the crosslinked temperature-responsive polymer.

(Temperature-responsive polymer)

Preferred examples of the temperature-responsive polymer to be used in the present invention may include: e.g., poly N-substituted acrylamide derivative, poly N-substituted methacrylamide derivative, and these copolymers; polyvinyl methyl ether, polypropylene oxide, polyethylene oxide, etherified methyl cellulose, partially acetylated polyvinyl alcohol, etc. Particularly preferred examples thereof to be used in the present invention may include: poly N-substituted acrylamide derivative or poly N-substituted methacrylamide derivative or these copolymers, polyvinyl methyl ether, polypropylene oxide, partially acetylated polyvinyl alcohol.

Preferred examples of the polymer to be used in the present invention is exemplified below in a sequence of from one having a lower LCST to one having a higher LCST:

poly-N-acryloyl piperidine;
poly-N-n-propyl methacrylamide;
poly-N-isopropyl acrylamide;
poly-N,N-diethyl acrylamide;
poly-N-isopropyl methacrylamide;
poly-N-cyclopropyl acrylamide;
poly-N-acryloyl pyrrolidine;
poly-N,N-ethyl methyl acrylamide;
poly-N-cyclopropyl methacrylamide;
poly-N-ethyl acrylamide The above polymer may be either a homopolymer or a copolymer comprising a monomer constituting the above polymer and "another monomer". The "another monomer" to be used for such a purpose may be either a hydrophilic monomer, or a hydrophobic monomer.

Specific examples of the above hydrophilic monomer may include: N-vinyl pyrrolidone, vinyl pyridine, acrylamide, methacrylamide, N-methyl acrylamide, hydroxyethyl methacrylate, hydroxyethyl acrylate, hydroxymethyl methacrylate, hydroxymethyl acrylate, methacrylic acid and acrylic acid having an acidic group, and salts of these acids, vinylsulfonic acid, styrenesulfonic acid, etc., and derivatives having a basic group such as N,N-dimethylaminoethyl methacrylate, N,N-diethylaminoethyl methacrylate, N,N-dimethylaminopropyl acrylamide, salts of these derivatives, etc. However, the hydrophilic monomer to be usable in the present invention is not restricted to these specific examples.

On the other hand, specific examples of the above hydrophobic monomer may include: acrylate derivatives and methacrylate derivatives such as ethyl acrylate, methyl methacrylate, butyl methacrylate, and glycidyl methacrylate; N-substituted alkyl methacrylamide derivatives such as N-n-butyl methacrylamide; vinyl chloride, acrylonitrile, styrene, vinyl acetate, etc. However, the hydrophobic monomer to be usable in the present invention is not restricted to these specific examples.

In general, when the above temperature-responsive polymer is copolymerized with a hydrophilic monomer, the resultant LCST may be increased. On the other hand, when the above temperature-responsive polymer is copolymerized with a hydrophobic monomer, the resultant LCST may be decreased. Accordingly, the liquid-gel transition temperature of a dispersion of the temperature-responsive polymer to which a crosslinked structure has been imparted according to the present invention is increased by using a temperature-responsive polymer which has been copolymerized with a hydrophilic monomer, and the liquid-gel transition temperature is decreased by using a temperature-responsive polymer which has been copolymerized with a hydrophobic monomer. Accordingly, it is also possible to control the liquid-gel transition temperature in the present invention by selecting the monomer component to be used for such copolymerization.

As the method of imparting a crosslinked structure to a temperature-responsive polymer, there are a method wherein a crosslinked structure is introduced into the polymer at the time of the polymerization of the monomer for providing the temperature-responsive polymer; and a method wherein a crosslinked structure is introduced to a temperature-responsive polymer after the completion of the polymerization of the monomer. In the present invention, however, it is possible to adopt each of these methods.

The former method can generally be conducted by utilizing the copolymerization with a bifunctional monomer (or a monomer having three or more functional groups). For example, such a method may be conducted by using a bifunctional monomer such as N,N-methylene bis-acrylamide, hydroxyethyl dimethacrylate, and divinylbenzene.

The latter method can generally be conducted by forming a crosslink between molecules by utilizing light, electron beam, γ-ray irradiation, etc.

Further, the latter method may also be conducted by crosslinking a temperature-responsive polymer, e.g., by using, as a crosslinking agent, a multi-functional molecule having a plurality of functional group (such as isocyanate group) which is capable of being bonded to a functional group (such as amino group) in the temperature-responsive polymer.

(Ratio of volume change)

With respect to the ratio (magnification) of the volume change in the support according to the present invention in water, when the volume of the shrunk support at a temperature higher than the LCST is defined as "1" (one), the equilibrium swelling volume of the support at a temperature for growing or regenerating a plant, which is lower than the LCST, may preferably be 1.1–100, more preferably 5–100. Herein, the "equilibrium swelling volume" refers to the volume which has been provided after the support according to the present invention is soaked in an excess of water at a predetermined temperature (constant temperature) for at least three days so that the swelling thereof reaches an equilibrium. With respect to such an equilibrium swelling volume, e.g., a paper of T. Tanaka, et al., Phys. Rev. Lett. 55, 2455 (1985) may be referred to.

The above-mentioned ratio of the temperature-dependent volume change of the support according to the present invention is generally dependent on the crosslinked structure thereof, particularly the crosslinking density, and has a tendency such that as the crosslinking density becomes lower, the volume change becomes larger. The crosslinking density can arbitrarily be controlled, e.g., by changing the copolymerization ratio of the bifunctional monomer in the former method, and e.g., by changing the quantity of irradiation with light, electron beam, γ-ray, etc., in the latter method.

The preferred range of the crosslinking density may be about 0.2 mol % to about 10 mol %, more preferably about 0.5 mol % to about 4 mol %, in terms of the ratio of the moles of branching points to the moles of all the monomer. When the crosslinked structure is introduced by using the former method, the copolymerization weight ratio of the bifunctional monomer to that of all the monomers (inclusive of the bifunctional monomer per se) may preferably be in the range of about 0.3 wt. % to about 3 wt. % (more preferably about 0.5 wt. % to about 1.5 wt. %).

In the present invention, when the crosslinking density exceeds the above-mentioned range of about 0.2 mol % to about 10 mol %, the ratio of the temperature-dependent volume change in the support according to the present invention is reduced, whereby clear liquid-gel conversion is less likely to occur. On the other hand, when the crosslinking density is below the above-mentioned range, the mechanical strength of the support according to the present invention is reduced, and the dispersion thereof is less likely to retain a strength enough to support a plant in a gel state thereof.

(Dimension and manufacturing method for support)

The dimension of the-support according to the present invention can appropriately be selected depending on the kind and dimension of a plant to be grown or regenerated. When the support has a particle shape or a micro-bead shape, the support may preferably have a particle size in the range of 0.1 μm to 1 cm (more preferably 1 μm to 1 mm) at the time of the shrinkage of the support in an aqueous dispersion, i.e., at a temperature higher than the LCST of the temperature-responsive polymer constituting the support.

Particularly, when the support has a particle shape or a micro-bead shape, it is preferred to use an emulsion polymerization method, a suspension polymerization method, a precipitation polymerization method, etc. As the method of imparting a crosslinked structure to the temperature-responsive polymer, it is possible to use a method wherein crosslinking is effected by using a bifunctional monomer at the time of the polymerization of a monomer; a method wherein the polymerization of a monomer is completed and the resultant product is shaped, and thereafter crosslinking is effected by using light, electron beam, γ-ray irradiation, etc., as described hereinabove.

Particularly, a reverse-phase suspension polymerization method may preferably be used, when the crosslinked temperature-responsive polymer in the form of micro-beads is synthesized from a water-soluble monomer and a water-soluble bifunctional monomer.

In the reverse-phase suspension polymerization method, it is preferred to use, as a dispersion medium, an organic solvent which does not dissolve the monomer and the produced polymer. For example, a saturated hydrocarbon such as hexane may preferably be used. Further, it is also possible to use a surfactant (e.g., a nonionic surfactant such as sorbitan fatty acid ester) as a suspension auxiliary in combination with the above organic solvent. The particle size of the micro-bead to be obtained can be controlled by the kind or amount of the surfactant to be added, the stirring speed, etc. As the polymerization initiator, it is possible to use either of a water-soluble polymerization initiator, and water-insoluble polymerization initiator. In view of effective collection or recovery of the polymerization product, it is preferred to perform the polymerization at a temperature lower than the LCST of the above temperature-responsive polymer, and therefore a low-temperature polymerization initiator such as redox polymerization initiator may preferably be used.

When the support according to the present invention is formed into a fiber shape, a flake shape, a sponge shape, a particle shape, etc., for example, it is possible to use a method wherein an aqueous solution of a temperature-responsive polymer which has been cooled to a temperature lower than the LCST thereof is extruded into water at a temperature higher than the LCST, or into an organic solvent which is unmixable with water by using a die. When such a shaping method is used, a crosslinked structure may be imparted to the polymer by using irradiation with light, electron beam, γ-ray, etc.

When the support according to the present invention is formed into a plate shape or a film shape, for example, it is possible to use a method wherein the above temperature-responsive polymer is dissolved in an organic solvent or water at a temperature lower than the LCST, and is shaped by a solvent casting method. When such a shaping method is used, a crosslinked structure may also be imparted to the polymer by using irradiation with light, electron beam, γ-ray, etc.

Further, it is also possible to mechanically crush either of the resultant shaped products having various shapes obtained by the above methods so as to shape the product into a support having a desired dimension.

In the present invention, it is possible to appropriately select the dispersion concentration, in a culture medium for culturing a plant, of the support comprising the temperature-responsive polymer having the above crosslinked structure, depending on the kind and shape of the plant. The concentration, however, may generally be 0.1–30 wt. %, more preferably 1–10 wt. %.

(Process for growing/regenerating plant)

The application of the polymer support or carrier according to the present invention to the process for growing or regenerating a plant is not particularly limited, but the carrier according to the present invention is particularly effectively usable in the application of the root-originating step of a plant. Hereinbelow, there is described an example of such a root-originating step of a plant.

Thus, a polymer for providing a network structure (e.g., in a particulate shape) is added into a desired culture medium for constituting a carrier according to the present invention so as to provide an M/G ratio which is not larger than the equilibrium culture medium absorption, and the polymer is caused to completely absorb the culture medium, thereby to cause the polymer to form a gel state. The dispersion concentration of the polymer support in the culture medium may appropriately be selected depending on the kind of the culture medium, and the kind, shape, dimension, etc., but in general, the concentration may preferably be 0.1–30 wt. %, more preferably 1.0–10 wt. %.

Subsequently, an organ or seedling of a plant such as leaf, stem, root, petal, and anther (pollen) is disposed on or inserted into the above gel, and is cultured under a condition under which the gel state is retained, thereby to originate a root in the gel. At this time, as described hereinabove, the regenerated root is grown while it pushes the carrier particles apart, and the regenerated root is completely shielded or screened from the external environment by the carrier, and therefore the propagation of bacteria and fungi is suppressed.

(Growth or regeneration of plant using support according to first embodiment)

Hereinbelow, there is described a preferred example of the process for growing or regenerating a plant by using the above support according to the first embodiment.

First of all, the above-mentioned polymer support is uniformly dispersed in a desired culture medium. Then, into the resultant culture medium dispersion of the polymer support, a plant organ such as leaf, stem, root, petal, anther (pollen), and seedling, or a plant tissue such as callus, hair root and protoplast which has been regenerated from the above plant is mixed and dispersed. The support absorbs the culture medium, and the volume thereof is increased, and the fluidity thereof is markedly reduced so as to be converted into a gel state. Accordingly, it is possible that the plant is supported in the gel and the plant is grown or regenerated therein.

On the other hand, the collection (or recovery) or transfer of the plant which has been grown or regenerated in the gel may easily be effected by adding an excess of water or a culture medium (water or culture medium in an amount of preferably 1.1–100 times, more preferably 1.5–10 times in terms of weight ratio based on the weight of the swollen gel) onto the gel of the support so as to again disperse the support to be liquidized. Particularly, when the root-originating plant is collected or transferred, the root-originating plant may easily be separated without damaging the plant. Herein, in the case of the polymer support according to the present invention, the liquid-gel conversion can appropriately be controlled as described above, and this feature is important as compared with the agar gel as described hereinabove.

Conventionally, the operation for separating the plant after the completion of the root-originating stage thereof from the agar gel has been a primary cause for the reduction in the efficiency of active root anchoring of the plant after such an operation. However, as described above, the polymer support according to the present invention can completely solve such problems.

In addition, the supplement of a nutrient which becomes insufficient in the above gel culture medium, or the removal of a waste material capable of inhibiting the growth or regeneration can also be performed by liquidizing the old gel to be removed in the above manner, and then transferring the plant into a fresh culture medium. In the present invention, the gel culturing may easily be continued in such a manner.

Further, in the case of the above support, after the plant is grown or regenerated and then collected or transferred, the support may easily be recovered from the dispersion liquid of the support (by a method such as centrifugal separation), the support is washed, whereby the resultant support can be recycled.

(Growth or regeneration of plant using support according to second embodiment)

Hereinbelow, there is described an example of the process for growing or regenerating a plant by using the above-mentioned (temperature-responsive) support according to the second embodiment.

When the temperature-responsive polymer is used as a support, the polymer support is uniformly dispersed at a temperature higher than the liquid-gel transition temperature of the support, and then the temperature is decreased to a value lower than the liquid-gel transition temperature, whereby uniform gel is formed on the basis of the water absorption and swelling of the polymer. Onto the resultant gel, an organ or seedling of a plant such as leaf, stem, root, petal, and anther (pollen) is disposed or inserted, and the plant is cultured while retaining the gel state and the plant is caused to originate a root in the gel. When the root-originating plant is collected or transferred from the gel, the gel is liquidized by raising the temperature to a value higher than the liquid-gel transition temperature so as to cause the dehydration and shrinkage of the crosslinked polymer, and then the root-originating plant may easily be separated from the dispersion of the shrunk carrier without damaging the plant. Herein, in the case of the polymer support according to the present invention, the liquid-gel conversion can appropriately be controlled as described above, and this feature is important as compared with the agar gel as described hereinabove.

Further, at a temperature higher than the LCST, the above polymer is in a dehydrated and shrunk state, and therefore the viscosity of the culture medium dispersion containing the support comprising the polymer is substantially equivalent to the viscosity of the culture medium per se. Due to such a characteristic, not only the collection and transfer of the plant are facilitated, but also the removal of the culture medium by washing at the time of the collection and transfer is simplified, and further, the collection and transfer operations do not damage the plant at all.

In addition, the supplement of a nutrient which becomes insufficient in the above gel culture medium, or the removal of a waste material capable of inhibiting the growth or regeneration can also be performed by liquidizing the gel at a temperature higher than the LCST to be removed together with the old culture medium. If a fresh culture medium is added to the culture medium, the gel culturing may easily be continued, or alternatively, the resultant plant as such may be transferred to the cultivation in a field or farm, whereby an epochal saving of labor in the transferring operations can be accomplished.

Further, in the case of the above support, after the plant is grown or regenerated and then collected or transferred, the support may easily recovered selectively from the dispersion liquid thereof (by a method such as centrifugal separation), the support is washed, whereby the resultant support can be recycled.

Hereinbelow, the present invention will be described in more detail with reference to Examples. However, it should be noted that the present invention is defined by Claims, but is not limited by the following Examples.

EXAMPLES

Example 1

(Synthesis of micro-bead support)

7.5 g of acrylamide, 0.1 g of N,N'-methylenebis-acrylamide, and 0.1 g of ammonium persulfate were dissolved in 100 mL (milliliter) of distilled water. The resultant aqueous solution was added into a solution which had been obtained by dissolving 10 g of sorbitan mono-oleate (SPAN-80, mfd. by Kanto Kagaku K.K.) in 1000 mL of hexane, and the resultant mixture was vigorously stirred under a nitrogen stream so as to form a suspension. Thereafter, 3 mL of N,N,N',N'-tetramethyl ethylenediamine was added to the resultant mixture, and subjected to polymerization for 4 hours at room temperature. The resultant aqueous phase was separated from the reaction mixture, and the polymerization product was washed with 500 mL of hexane three times. Subsequently, 1000 mL of distilled water was added to the polymerization product and then stirred, and thereafter the mixture was left standing so as to precipitate a carrier in the form of micro-beads, and the supernatant liquid was discarded. Such a water-washing operation was repeated three times, and then the product was dried under vacuum, thereby to obtain 7 g of a support (A) in the form of micro-beads according to the present invention.

When the above support in distilled water was observed with an optical microscope, spherical particles having a diameter of about 20–200 μm were observed.

Example 2

A piece of lateral bud tissue of carnation was cut out, and washed with detergent and aqueduct water, and immersed in 70% aqueous ethanol solution for 30 sec., and immersed in 1% aqueous sodium hypochlorite solution for 7 min., to be sterilized, and further was washed with sterilized distilled water several times. The thus obtained lateral bud as an explant was planted on an MS-culture medium (Murashige-Skoog culture medium, mfd. by Cosmo-Bio Co.) containing 0.8% of agar, and cultured at 25° C. for two weeks so as to form a shoot, and then the shoot was cut into pieces thereof corresponding to the respective nodes.

Subsequently, 0.5 g of the micro-bead support (A) prepared in Example 1 was dispersed in 10 mL of an MS-culture medium containing 0.1 mg/L of 1-naphthalene acetic acid, and 10 g/L of sucrose in terms of the respective concentration, and poured into a tube made of glass (culturing vessel) having an inside diameter of 2 cm and a length of 10 cm, and sterilized by an autoclave treatment (121° C., for 20 minutes), and simultaneously the above support was swollen with the above MS-culture medium and formed into a gel state.

On the thus obtained gel, the above-mentioned shoots of the carnation which had been cut into pieces corresponding to the respective nodes were transferred. As a result, the shoots were well retained in the above gel. Further, when culturing was conducted for three weeks in such a state, the origination of roots in the gel was observed.

Then, when the thus obtained root-originating plant was collected from the culturing vessel for the purpose of acclimation (or acclimatization) thereof, 15 mL of water was added into the culture vessel containing the root-originating plant. As a result, the above micro-bead support was immediately dispersed and the dispersion culture medium was converted form the gel state to a liquid state, whereby the root-originating plant could easily be taken out from the culture vessel. In the above-mentioned collecting step, the support (A) attached to the roots could easily be removed therefrom by washing with water, no damage to the roots was observed, and the operations per se were very easy.

Comparative Example 1

An MS-culture medium-containing 8 g/L of agar, 0.1 mg/L of 1-naphthaleneacetic acid, and 10 g/L of sucrose in terms of their concentrations was prepared by an ordinary method, and was then sterilized by an autoclave treatment. Subsequently, the culture medium was cooled to 23° C. to be formed into a gel state, and thereafter, the shoot of the carnation which had been cut into pieces corresponding to its respective nodes was transferred onto the thus obtained gel, and was subjected to a culture process in the same manner as in Example 2 for 3 weeks. After three weeks counted from the initiation of the culture process, it was recognized that roots were originated in the gel.

In order to separate the root-originating plant from the gel, the plant was taken out from the culture vessel under a state under which the gel was attached to the roots, and then was mechanically shaken in water by an ordinary method. As a result, it was difficult to remove the gel from the hair-like roots, but some of the hair-like roots were broken off by an operation of removing the gel by use of hands. Further, the washing operation using hands was very troublesome.

Example 3

(Synthesis of micro-bead support)

15 g of N-isopropyl acrylamide (NIPAAm), 0.1 g of N,N'-methylenebis-acrylamide (Bis), and 0.1 g of ammonium persulfate were-dissolved in 100 mL of distilled water. The resultant aqueous solution was added into a solution which had been obtained by dissolving 10 g of sorbitan mono-oleate (SPAN-80, mfd. by Kanto Kagaku K.K.) in 1000 mL of hexane, and the resultant mixture was vigorously stirred under a nitrogen stream so as to form a suspension.

Thereafter, 3 mL of N,N,N',N'-tetramethylethylene diamine was added to the resultant mixture, and subjected to polymerization for 4 hours at room temperature.

The resultant aqueous phase was separated from the reaction mixture, and the polymerization product was washed with 500 mL of hexane three times. Subsequently, 1000 mL of distilled water was added to the polymerization product, and was cooled to 4° C. Thereafter, the mixture was heated up to 40° C. so as to shrink the resultant carrier in the form of micro-beads, and the supernatant liquid was discarded. Such a water-washing operation was repeated three times, and then the product was dried under vacuum, thereby to obtain a support (B) in the form of micro-beads according to the present invention.

The above procedure was repeated except for using 0.4 g of Bis, thereby to obtain a support (C) in the form of micro-beads according to the present invention.

The diameters of the-support (B) and (C) were measured under an optical microscope at various temperatures. The thus obtained results are shown in the graph of FIG. 1. In addition, these diameters are converted into ratios of volume change (magnifications) in terms of the ratio of the volume to the volume (=1 (one)) of the shrunk micro-bead. The thus obtained results are shown in the graph of FIG. 2. FIG. 3 (Table 1) shows data corresponding to those of the above FIGS. 1 and 2.

(Preparation of support dispersion)

5 g of the dried support (B) obtained by the above procedure was dispersed in 100 mL of a Murashige-Skoog culture medium for a plant (MS-culture medium, mfd. by Cosmo-Bio K.K.) at 40° C. When the resultant dispersion was gradually cooled, the dispersion lost its fluidity at about 31° C. to be formed into a gel state. When the product in the gel state was gradually warmed, the gel again returned to a dispersion liquid having a fluidity at about 32° C.

Example 4

A piece of lateral bud tissue of carnation was cut out, and washed with detergent and aqueduct water, and immersed in 70% aqueous ethanol solution for 30 sec., and immersed in 1% sodium hypochlorite solution for 7 min., to be sterilized, and further washed with sterilized distilled water several times. The thus obtained lateral bud tissue as an explant was planted on an MS-culture medium containing 0.8% of agar, and cultured for two weeks so as to form a shoot, and then the shoot was cut into pieces thereof corresponding to the respective nodes.

Subsequently, 5 g of the micro-bead support (B) prepared in Example 3 was dispersed in 100 mL of an MS-culture medium containing 0.1 mg/L of 1-naphthalene acetic acid, and 10 g/L of sucrose in terms of the respective concentrations. The resultant dispersion medium was sterilized by an autoclave treatment (121° C., for 20 minutes).

The dispersion medium of the support (B) obtained above assumed a liquid state at 37° C., but was formed into a complete gel state by lowering the temperature to about 23° C. After the dispersion medium of the support (B) was formed into a complete gel state in such a manner, the above-mentioned shoots of the carnation which had been cut into pieces corresponding to the respective nodes were transferred onto the thus obtained gel. When culturing was conducted for three weeks at about 23° C., the origination of roots in the gel was observed after three weeks counted from the initiation of the culturing.

Then, when the thus obtained root-originating plant was collected from the culturing vessel for the purpose of acclimation thereof, the temperature of the culture vessel containing the root-originating plant was raised up to about 37° C., the volume of the above micro-bead support was immediately reduced and the dispersion culture medium was converted form the gel state to a liquid state, whereby the root-originating plant could easily be taken out from the culture vessel. In the above-mentioned collecting step, the support (B) attached to the roots could easily be removed therefrom by washing with water, no damage to the roots was observed, and the operations per se were very easy.

Comparative Example 2

An MS-culture medium containing 8 g/L of agar, 0.1 mg/L of 1-naphthaleneacetic acid, and 10 g/L of sucrose in terms of their concentrations was prepared by an ordinary method, and was then sterilized by an autoclave treatment. Subsequently, the resultant culture medium was cooled to about 23° C. to be formed into a gel state, and thereafter, the shoot of the carnation which had been cut into pieces corresponding to its respective nodes was transferred onto the thus obtained gel, and was subjected to culturing in the same manner as in Example 4 at about 23° C. for 3 weeks. After three weeks counted from the initiation of the culturing, it was recognized that roots were originated in the gel.

In order to separate the root-originating plant from the gel, the plant was taken out from the culture vessel under a state under which the gel was attached to the roots, and then was mechanically shaken in water by an ordinary method. As a result, it was difficult to remove the gel attached to the hair-like roots from these roots, but some of the hair-like roots were broken off by an operation of removing the gel by use of hands. Further, the washing operation using hands was very troublesome.

Example 5

A stem of tobacco (Nicotina glutinosa) which had been grown for four to five months was cut so as to provide a piece thereof having a length of 4–5 cm, and washed with detergent and aqueduct water, and immersed in 70% aqueous ethanol solution for 30 sec., and immersed in 1% sodium hypochlorite solution for 7 min., to be sterilized, and was further washed with sterilized distilled water several times.

Then, the above stem was cut by using a sterilized razor blade so as to provide a piece thereof having a length of about 5 mm. A cork borer having a diameter of about 3 mm was stuck to the resultant slice so as to collect a marrow tissue thereof, and then the marrow tissue was further cut into pieces of about 2–3 mm. All of the above-mentioned operations were conducted under sterilized conditions.

Subsequently, 5 g of the support (B) in the form of micro-beads according to the present invention prepared in Example 3 was dispersed in 100 mL of a culture medium for tobacco cell culture containing no agar (Atsushi Hirai, et al., Seibutsukagaku Jikken-ho (Methods of Biochemistry) 16, "Shokubutsu Saibo Ikushu Nyuumon (Introduction to Hybridization of Plant Cells)", p. 15, (1969), published by Gakkai-Shuppan Center) at 37° C., and was sterilized by an autoclave treatment.

Several slices of the marrow tissue obtained by the above method were dispersed in the culture medium containing the above support in the form of micro-bead at 37° C. Thereafter, the temperature was lowered to about 23° C. so as to convert the culture medium into a complete gel state, whereby the marrow tissue was embedded in the gel. When the resultant gel was subjected to culturing for 15 days under artificial light irradiation condition of 1000–3000 luxes, good callus formation from the respective marrow tissue pieces was observed.

Then, in order to collect the callus which had been formed in the gel, the gel was heated up to 37° C. for about 3 minutes so as to dissolve the gel, and thereafter the resultant mixture was moderately centrifuged so as to isolate the callus. Further, a 0.5M-mannitol solution was added to the callus to be again formed into a suspension, and the resultant product was moderately centrifuged, thereby to provide tobacco callus from which the above support (B) had been removed completely.

Example 6

With respect to each of dried Sumicagel S-50 (mfd. by Sumitomo Kagaku Kogyo K.K., poly (acrylic acid-vinyl alcohol) copolymer, spherical shape, diameter=180–290 $\mu$m) and dried Aquaric CA-H (mfd. by Nippon Shokubai K.K., crosslinked polyacrylic acid product, indeterminate bulk shape, dimension=1–3 mm), the equilibrium water absorption was measured in each of distilled water, physiological saline solution, and a culture medium for a plant (MS-culture medium) at room temperature, thereby to obtain results as shown in FIG. 4 (Table 2).

Example 7

0.32 g of the dried Sumicagel S-50 used in Example 6 was added to and dispersed in 8 mL of an MS-culture medium having a sucrose concentration of 2 wt. %, and poured into a test tube (diameter=18 mm, length=100 mm) and was left standing at room temperature. As a result, the dried Sumicagel S-50 completely absorbed the culture medium to be converted into a gel state. The M/G ratio in this Example was 25, and was also 25% of the equilibrium culture medium absorption (100) of the Sumicagel S-50 (measured in Example 6).

0.08 mL of a liquid wherein various germs had been propagated (various germ concentration: 1,000 germs/mL) was added onto the surface of the above-mentioned gel. The various germ-propagated liquid was completely absorbed into the above gel carrier. When the culturing was conducted in this state at about 25° C., for 3 days, the colonies of the germs were observed on the surface of the gel, but apparently, the penetration of germs into the interior of the gel was not recognized.

Example 8

0.18 g of the dried Aquaric CA-H used in Example 6 was added to and dispersed in 8 mL of an MS-culture medium having a sucrose concentration of 2 wt. %, and poured into a test tube (diameter=18 mm, length=100 mm) and was left standing at room temperature. As a result, the Aquaric CA-H completely absorbed the culture medium to be converted into a gel state. The M/G ratio in this Example was 44.4, and was also 44.4% of the equilibrium culture medium absorption (100) of the Aquaric CA-H (measured in Example 6).

0.08 mL of the various germ-propagated liquid used in Example 7 was added onto the surface of the above-mentioned gel. The various germ-propagated liquid was completely absorbed into the above gel carrier. When the culturing was conducted in this state at about 25° C. for 3 days, colonies of the germs were somewhat observed on the surface of the gel, but apparently, the penetration of germs into the interior of the gel was not recognized.

Comparative Example 3

0.064 g of agar was added to 8 mL of an MS-culture medium having a sucrose concentration of 2 wt. % and then boiled so as to dissolve the agar in the culture medium. Immediately thereafter, the resultant mixture was poured into a test tube (diameter=18 mm, length=100 mm) and was left standing at room temperature to be converted into a gel state.

0.08 mL of the various germ-propagated liquid used in Example 7 was added onto the surface of the above-mentioned agar gel, and cultured at about 25° C. As a result, the liquid containing the various germs was not absorbed into the agar gel, and 3 days after, the propagation of the germs covering the entire surface of the gel was observed.

Comparative Example 4

8 mL of an MS-culture medium having a sucrose concentration of 2 wt. % was poured into a test tube (diameter=18 mm, length=100 mm). 0.08 mL of the various germ-propagated liquid used in Example 7 was added to the culture medium, and cultured at about 25° C. As a result, 3 days after, the culturing liquid became whitely turbid, and marked propagation of the germs was observed.

Example 9

15 g of N-isopropyl acrylamide (NIPAAm, mfd. by Kojin K.K.), 0.47 g of acrylic acid, 0.1 g of N,N'-methylenebis-acrylamide (Bis), 0.2 g of ammonium persulfate, 6.6 mL of 1N-NaOH, and 0.1 mL of N,N,N',N'-tetramethylethylene diamine were dissolved in 90 mL of distilled water. The resultant mixture was subjected to polymerization for 4 hours at room temperature, thereby to obtain a poly-N-isopropyl acrylamide (PNIPAAm) hydrogel having a crosslinked structure.

The resultant gel was mechanically crushed by means of a mixer, thereby to prepare indeterminately shaped blocks (C-PNIPAAm-H). The C-PNIPAAm-H was dispersed in one liter of distilled water and cooled to 4° C. Thereafter, the resultant mixture was warmed to 50° C. so as to shrink the C-PNIPAAm-H, and the resultant supernatant liquid was discarded. Such a washing operation was repeated two times, thereby to remove the unreacted monomer and the remaining polymerization initiator. Further, the C-PNIPAAm-H was dried under vacuum.

The equilibrium culture medium absorption of the thus obtained C-PNIPAAm-H was considerably different depending on the condition whether the temperature was above or below the lower limit critical solution temperature (LCST, in the neighborhood of 30° C.) of PNIPAAm, and was about 90 at 25° C., and about 2.0 at 35° C. in a Hyponex culture medium (Hyponex 7-6-19, mfd. by Hyponex Japan K.K.).

Example 10

In a test tube (diameter=20 mm, length=150 mm), 0.4 g of the C-PNIPAAm-H obtained in Example 9 was mixed with and dispersed in 20 mL of a liquid medium (having a composition as shown in FIG. 5 (Table 3)), and left standing at room temperature. As a result, the C-PNIPAAm-H completely absorbed the liquid medium to be formed into a gel state.

On the surface of the above gel, two plantlets of YT-57 (Cym. LOVELY ANGEL "The Two Vergins") which had been grown so as to provide a leaf length of 4 cm were transferred, and were cultured in a culture chamber (25° C., 3000 lux, 16h-fluorescent light illumination) under a non-sterilized condition. Even after two months counted from the initiation of the culturing, apparently, the contamination due to various germs was not recognized on the gel surface and in the interior of the gel, and the plantlets were smoothly grown so as to provide a leaf length of 10 cm.

Comparative Example 5

In a test tube (diameter=20 mm, length=150 mm), 0.12 g of agar was added to 20 mL of the liquid medium used in Example 10, and the resultant mixture was boiled so as to dissolve the agar in the culture medium, and thereafter was left standing at room temperature, thereby to form an agar gel.

On the surface of the above gel, two plantlets of YT-57 which had been grown so as to provide a leaf length of 4 cm were transferred in the same manner as in Example 10, and was cultured in a culture chamber (25° C., 3000 lux, 16h-fluorescent light illumination) under a non-sterilized condition. After one week counted from the initiation of the culturing, the propagation of various germs was recognized on the agar gel surface. After one month counted from the initiation of the culturing, the contamination was recognized at the base portion of the plant and along the roots thereof which had been grown in the agar gel, and the growth of the plantlets was strongly suppressed.

Example 11

In a test tube (diameter=20 mm, length=200 mm), 0.4 g of the C-PNIPAAm-H obtained in Example 9 was mixed with and dispersed in 20 mL of a Hyponex culture medium (Hyponex 7-6-19, mfd. by Hyponex Japan K.K, 3.5 g/L) containing 20 g/L of sucrose, and 100 g/L of banana. The resultant mixture was then sterilized by an autoclave treatment (121° C., 1.2 Kg/cm$^2$, for 20 minutes), and left standing at room temperature. As a result, the polymer completely absorbed the culture medium to be formed into a gel state.

On the surface of the above gel, two plantlets of YT-57 which had been grown so as to provide a leaf length of 2 cm were transferred, and were cultured in a culture chamber (25° C., 3000 lux, 16h-fluorescent light illumination) under a sterilized condition. After three months counted from the initiation of the culturing, the plantlets were grown so as to provide a length of about 10 cm. During the three-month culturing, water was absorbed into the plantlets or evaporated, whereby the level of the culture medium surface was lowered. When 10 mL of a Hyponex solution (Hyponex 7-6-19, 2 g/L) was further supplemented sterilizedly to the gel, the supplemented solution was completely absorbed into the above gel, and the level of the culture medium surface was raised. Thereafter, the growth of the plantlets was markedly promoted as compared with that in the case of a similar example provided with no supplemental fertilizer.

Comparative Example 6

In a test tube (diameter=20 mm, length=200 mm), 0.12 g of agar was mixed with and dispersed in 20 mL of a Hyponex culture medium used in Example 11, and sterilized by an autoclave treatment and the agar was simultaneously dissolved, and left standing at room temperature, thereby to form a gel.

On the surface of the above gel, two plantlets of YT-57 (Cym, LOVERY ANGEL, "The Two Vergins") which had been grown so as to provide a leaf length of 2 cm were transferred, and were cultured in a culture chamber (25° C., 3000 lux, 16h-fluorescent light illumination) under a sterilized condition. After three months counted from the initiation of the culturing, the seedings were grown so as to provide a length of about 10 cm. During the three-month culturing, water was absorbed into the plantlet or evaporated, whereby the level of the culture medium surface was lowered. When 10 mL of a Hyponex solution (Hyponex 7-6-19, 2 g/L) was further supplemented sterilizedly to the agar gel, the supplemented solution was not absorbed into the agar gel, and the level of the culture medium surface was not raised. As a result, the base portion of the plant was placed below the level of culture medium surface.

Example 12

In a plant box (Shibata Hario K.K., made of polycarbonate, upper part:=75×75 mm, lower part 65×65 mm, height=100 mm), 2.1 g of the C-PNIPAAm-H prepared in Example 9 was mixed with and dispersed in 105 mL of a Hyponex culture medium used in Example 11, and was sterilized by an autoclave treatment (121° C., 1.2 Kg/cm$^2$, 20 minutes), and left standing at room temperature. As a result, the C-PNIPAAm-H completely absorbed the culture medium to be converted into a gel state. The M/G ratio thereof was 56% of the equilibrium culture medium absorption of the C-PNIPAAm-H.

On the surface of the above gel, 16 plantlets of YT-57 which had been grown so as to provide a leaf length of 2 cm were transferred, and were sterilizedly cultured in a culture chamber (25° C., 3000 lux, 16h-fluorescent light illumination). After three months counted from the initiation of the culturing, when the plantlets were grown so as to provide a length thereof of about 10 cm, the plant box was non-sterilizedly immersed in warm water at 35° C. for 20 minutes. As a result, the C-PNIPAAm-H was shrunk and almost all of the culture medium which had been contained in the carrier was discharged from the carrier.

The lid of the plant box was opened and the above discharged culture medium was sucked by using a dropping pipette, and then about 150 mL of aqueduct water at a temperature of about 16° C. was added to the plant box, whereby the aqueduct water was absorbed into the C-PNIPAAm-H. The temperature was again raised to about 35° C. to shrink the C-PNIPAAm-H, whereby the aqueduct water was discharged from the carrier. When the sugar concentration of the discharged aqueduct water was measured by means of a refractometer, the content was found to be below the detection limit thereof (0.2 wt. %).

The discharged aqueduct water was removed by using a dropping pipette, and about 105 mL of a liquid medium used in Example 10 was added to the plant box. Then, the plant box was non-sterilizedly subjected to culturing in a culture chamber (25° C., 3000 lux, 16h-fluorescent light illumination) under a condition such that the lid of the plant box was left open and the plant box was covered with a vinyl bag in which a hole having a diameter of 5 mm had been opened. Even after one month counted from the initiation of the culturing, the contamination of various germs was not recognized apparently, and the plantlets were smoothly grown.

At this time, the vinyl bag was taken off, and the plant box was immersed in warm water of 35° C. for 20 min. in the same manner as described hereinabove. As a result, the C-PNIPAAm-H was shrunk and discharged almost all of the culture medium which had been contained in the above carrier.

The discharged culture medium was removed, and about 105 mL of the liquid medium used in Example 10 was added to the plant box, and the plantlets were grown in a greenhouse, while aqueduct water was supplemented at intervals of 2–3 days with respect to the vaporized portion of water from the upper portion of the vessel. The plantlets were smoothly grown even after about 1 month, but the algal generation on the gel surface was recognized by the naked eye when the period of the culturing exceeded about 1.5 month. However, the plantlets showed smooth growth substantially without receiving the influence of the alga.

Further, at a point of time at which the period of the growth in the vinyl greenhouse exceeded 2 months, the plantlets were taken out from the above plant box, and transferred to a black vinyl pot having a diameter of about 9 cm, while Growell MO-2 (bark produced in New Zealand, available from Mukoyama Orchid Ltd.) was disposed around the plantlets, in a state such that the culture medium was as such attached to the roots of the plantlets. Thereafter, the pot was subjected to ordinary cultivation in a greenhouse.

After 3 months, when the state of the growth of the upper portion of the plant above the ground was investigated, it was found that the leaf width was large, the color of the leafs was thick, and further the base portion was thick, and the growth of the plantlets was very good.

Comparative Example 7

In a plant box used in Example 12, 0.63 g of agar and 105 mL of a Hyponex culture medium used in Example 12 were charged, and sterilized by an autoclave treatment, and left standing at room temperature, thereby to be formed into a gel.

On the surface of the above gel, 16 plantlets of YT-57 which had been grown so as to provide a leaf length of 2 cm were transferred, and were cultured in a culture chamber (25° C., 3000 lux, 16h-fluorescent light illumination) under a sterilized condition. After three months counted from the initiation of the culturing, the plantlets were grown so as to provide a length of about 10 cm. At this time, the lid of the plant box was opened and the culturing was conducted non-sterilizedly. As a result, after three days counted from the opening of the lid, the content in the plant box was contaminated with various germs. After one week, remarkable propagation of various germs was observed in most part of the agar gel and the portion around the base portion of the plant.

Example 13

In a Pack-Plast container (Tomohiro Trade K.K., cylindrical plastic vessel, inside diameter of upper part=110 mm, inside diameter of lower part=90 mm, height=75 mm), 4 g of the dried C-PNIPAAm-H prepared in Example 9 was mixed with and dispersed in 200 mL of a Hyponex solution (Hyponex 20-20-20, Hyponex Japan K.K., 1 g/L), whereby the C-PNIPAAm-H completely absorbed the solution to be formed into a gel state.

In the resultant gel, ten plantlets of an orchid, "RG310" (Cym. ENZAN SYMPHONY "RG310") which had been grown under a sterilized condition so as to provide a fresh weight of 0.25 g were transferred, were grown in a greenhouse under a condition such that the upper part of the Pack-Plast container was completely opened (i.e., under a non-sterilized condition). During this growth, a solution of the above Hyponex which had been diluted so as to provide double volume, as an additional fertilizer was supplied to the container from the upper part of the container so as to supplement a nutrient or water to be vaporized from the upper part of the container or to be absorbed into the plant.

The growth of the portion of the plantlet below the gel surface was somewhat slow, but the portion thereof above the gel surface was smoothly grown. FIG. 6 (Table 4) shows the results obtained by measuring the degree of the growth (fresh weight) of the plantlet after 48 days counted from the initiation of the cultivation.

Example 14

In a Pack-Plast container, 2 g of the dried C-PNIPAAm-H prepared in Example 9 was mixed with and dispersed in 100 mL of a Hyponex solution used in Example 13 in the same manner as in Example 13, whereby the C-PNIPAAm-H completely absorbed the solution to be formed into a gel state. Then, 100 mL of Growell MO-2 was impregnated with a large excess of a Hyponex solution, and then a part of the solution (gravitational water) which flowed out due to gravity was removed, and the resultant Growell was mixed into the above gel.

In the same manner as in Example 13, ten plantlets of an orchid, "RG310" which had been grown so as to provide a fresh weight of 0.25 g were transferred onto the resultant support (mixture of C-PNIPAAm-H and Growell MO-2) prepared above, and the plantlets were grown in a greenhouse under a condition such that the upper part of the Pack-Plast container was completely opened (i.e., under a non-sterilized condition). During this growth, a solution of the above Hyponex which had been diluted so as to provide double volume, as an additional fertilizer was supplied to the container from the upper part of the container so as to supplement a nutrient or water to be vaporized from the upper part of the container or to be absorbed into the plant.

Both of the portions of the above plantlets (portions thereof below the gel surface and above the gel surface) were smoothly grown. When the fresh weights of the plantlets after 48 days counted from the initiation of the cultivation were measured, the results as shown in FIG. 6 (Table 4) were obtained.

Comparative Example 8

200 mL of Growell MO-2 was charged into a Pack-Plast container used in Example 13, and was impregnated with a large excess of a Hyponex solution, and then a part of the solution (gravitational water) flowing out due to gravity was removed.

In the same manner as in Example 13, ten plantlets of an orchid, "RG310" which had been grown so as to provide a fresh weight of 0.25 g were transferred onto the resultant support, and the plantlets were grown in a greenhouse under a condition such that the upper part of the Pack-Plast container was completely opened, i.e., under a non-sterilized condition. During this growth, a solution of the above Hyponex which had been diluted so as to provide double volume, as an additional fertilizer was supplied to the container from the upper part of the container so as to supplement a nutrient or water to be vaporized from the upper part of the container or to be absorbed into the plant.

The above plantlets were slowly grown. When the fresh weights of the plantlets after 48 days counted from the initiation of the cultivation were measured, the results as shown in FIG. 6 (Table 4) were obtained. Industrial Applicability As described hereinabove, according to the present invention, there is provided a support for growing or regenerating a plant, comprising particles having a dimension in the range of 0.1 µm to 1 cm in a dried state, and comprising a hydrogel having a crosslinked structure. Particles of the crosslinked hydrogel having of the above-mentioned specific dimension have a property such that they are swollen in water or a culture medium so as to reversibly increase their volume to be converted into a gel state, and therefore various plants may be supported in the resultant gel and the plants therein may be grown or regenerated. On the other hand, when the plant is intended to be collected, an excess of water or culture medium is added to the gel so as to decrease the ratio of the volume of the support to that of the culture medium, whereby the plant-supporting ability of the support may be decreased and the above plant may easily be separated from the support.

When the above support is used, the embedding of the plant into the gel, the recovery of the plant from the gel, etc., may easily be conducted without damaging the plant at all, by regulating the volume ratio of the support to the water or culture medium. Therefore, according to the present invention, it is possible to solve the problems of the conventional gel culturing process using agar, etc.

Further, the present invention also provides a support for growing or regenerating a plant, comprising a polymer which has been obtained by crosslinking a temperature-responsive polymer having a LCST (lower critical solution temperature).

When the above support is used, the embedding of the plant into the gel, the recovery of the plant from the gel, etc., may easily be conducted without damaging the plant at all, e.g., by changing the temperature in a physiological temperature range of the plant. Therefore, according to the present invention, it is possible to completely solve the problems of the conventional gel culturing process using agar, etc.

The present invention further provides a carrier for growing or regenerating a plant, comprising a culture medium, and a polymer, wherein the culture medium is absorbed in and retained by the network structure comprising the above polymer substantially completely.

When the above carrier according to the present invention is used, it is possible to grow or regenerate a plant while effectively suppressing the propagation of bacteria and fungi, whereby the problems of the conventional gel culturing process using agar may be solved.

I claim:

1. A carrier for growing or regenerating a plant, comprising a polymer which has been obtained by crosslinking a temperature-responsive polymer having a LCST (lower critical solution temperature).

2. The carrier for growing or regenerating a plant according to claim 1, wherein the LCST is higher than 0° C. and not higher than 60° C.

3. The carrier for growing or regenerating a plant according to claim 1, which is in the form of: particles, microbeads, fibers, flakes, a sponge, a film or a plate.

4. The carrier for growing or regenerating a plant according to claim 1, which has a dimension in the range of 0.1 µm to 1 cm.

5. A method of growing or regenerating a plant, comprising:

dispersing a carrier for growing or regenerating a plant, which has been obtained by crosslinking a temperature-responsive polymer having a LCST (lower critical solution temperature), in a predetermined culture medium at a temperature higher than the LCST;

mixing a plant in the resultant dispersion; and lowering the temperature to a value lower than the LCST to reduce the fluidity of the dispersion and to convert the dispersion into a gel state, thereby to grow or regenerate the plant.

6. A method of growing or regenerating a plant, comprising:

dispersing a carrier for growing or regenerating a plant, which has been obtained by crosslinking a temperature-responsive polymer having a LCST (lower critical solution temperature), in a predetermined culture medium at a temperature higher than the LCST;

lowering the temperature to a value lower than the LCST to reduce the fluidity of the resultant dispersion and to convert the dispersion into a gel state; and disposing or inserting a plant on or in the gel, thereby to grow or regenerate the plant.

7. The method of growing or regenerating a plant according to claim 5, wherein the gel containing the grown or regenerated plant is again converted into a dispersion liquid of the carrier at a temperature higher than the LCST, thereby to recover and/or transfer the plant.

8. The method of growing or regenerating a plant according claim 5, wherein the plant which has been grown or regenerated at a temperature lower than the LCST is recovered and/or transferred from the dispersion liquid at a temperature higher than the LCST; the carrier is separated and recovered from the dispersion liquid; and thereafter the carrier is washed and sterilized, thereby to reuse the recovered carrier as a carrier for growing or regenerating a plant.

9. A support for growing or regenerating a plant, comprising a network structure material and a culture medium retained in the network structure material in a proportion of 10% to 100% of the equilibrium culture medium absorption; said network structure material having a dimension in the range of 0.1 $\mu$m to 1 cm in a dried state, and comprising a hydrogel having a crosslinked structure.

10. The support for growing or regenerating a plant according to claim 9, wherein a grown or regenerated tissue of the plant does not penetrate into the interior of the hydrogel having a crosslinked structure.

11. The support for growing or regenerating a plant according to claim 9, wherein the network structure material is in the form of: particles, micro-beads, fibers, flakes, a sponge, a film or a plate.

12. A method of growing or regenerating a plant, wherein a support is swollen with a culture medium in a culturing vessel so as to reduce the fluidity of the culture medium to be formed into a gel state, and to support a plant by the gel, thereby to grow or regenerate the plant, wherein the plant is grown or regenerated by using the support, and thereafter an excess of water is added to the support to increase the fluidity of the support, thereby to recover the plant, and the support comprises particles having a dimension in the range of 0.1 $\mu$m to 1 cm in a dried state, and comprising a hydrogel having a crosslinked structure.

13. A carrier for growing or regenerating a plant, comprising a culture medium and a polymer, wherein the culture medium is substantially absorbed into and retained by the network structure comprising the polymer.

14. The carrier for growing or regenerating a plant according to claim 13, wherein the network structure comprises a hydrogel having a crosslinked network structure which prevents the penetration thereinto of bacteria, fungi and/or a regenerated tissue of plant.

15. The carrier for growing or regenerating a plant according to claim 13, wherein the network structure material has a dimension in the range of 0.1 $\mu$m to 1 cm in a dried state, and the carrier is in the form of particles, micro-beads, fibers, a film, or a sheet-like shape.

16. A method of growing or regenerating a plant, wherein a carrier comprising a culture medium and a polymer constituting a network structure is used so as to grow or regenerate a plant while suppressing the propagation of bacteria and fungi; the culture medium being substantially absorbed into and retained by the network structure in a proportion of 10% to 100% of the equilibrium culture medium absorption of the polymer constituting the network structure.

17. The method of growing or regenerating a plant according to claim 6, wherein the gel containing the grown or regenerated plant is again converted into a dispersion liquid of the carrier at a temperature higher than the LCST, thereby to recover and/or transfer the plant.

18. The method of growing or regenerating a plant according to claim 6, wherein the plant which has been grown or regenerated at a temperature lower than the LCST is recovered and/or transferred from the dispersion liquid at a temperature higher than the LCST; the carrier is separated and recovered from the dispersion liquid; and thereafter the carrier is washed and sterilized, thereby to reuse the recovered carrier as a carrier for growing or regenerating a plant.

* * * * *